United States Patent
Jeong et al.

(10) Patent No.: US 12,419,478 B2
(45) Date of Patent: Sep. 23, 2025

(54) CLEANER STATION

(71) Applicant: LG ELECTRONICS INC., Seoul (KR)

(72) Inventors: Jeonghoon Jeong, Seoul (KR); Jungwan Ryu, Seoul (KR); Dongjae Lee, Seoul (KR); Ingyu Yang, Seoul (KR)

(73) Assignee: LG Electronics Inc., Seoul (KR)

( * ) Notice: Subject to any disclaimer, the term of this patent is extended or adjusted under 35 U.S.C. 154(b) by 1042 days.

(21) Appl. No.: 17/458,855

(22) Filed: Aug. 27, 2021

(65) Prior Publication Data

US 2022/0061618 A1    Mar. 3, 2022

(30) Foreign Application Priority Data

Aug. 27, 2020 (KR) .......................... 10-2020-0108778

(51) Int. Cl.
*A47L 9/28* (2006.01)
*A47L 9/14* (2006.01)
*A61L 2/10* (2006.01)

(52) U.S. Cl.
CPC ............. *A47L 9/2873* (2013.01); *A47L 9/149* (2013.01); *A61L 2/10* (2013.01); *A61L 2202/11* (2013.01); *A61L 2202/122* (2013.01)

(58) Field of Classification Search
CPC .................................................... A47L 9/2873
See application file for complete search history.

(56) References Cited

U.S. PATENT DOCUMENTS

| 2011/0214686 A1* | 9/2011 | Chavana, Jr. | A47L 9/2857 134/1 |
| 2015/0129781 A1* | 5/2015 | Kretschmann | A61L 2/10 250/492.1 |
| 2021/0010685 A1* | 1/2021 | Hackert | A47L 9/2873 |

FOREIGN PATENT DOCUMENTS

| AU | 2005-211645 A1 | 9/2006 |
| JP | 3822511 | 9/2006 |
| KR | 20070012109 | 1/2007 |
| KR | 100899785 | 5/2009 |
| KR | 20110111201 | 10/2011 |
| KR | 20120057595 A * | 6/2012 |

(Continued)

OTHER PUBLICATIONS

English Translation of KR 20120057595A provided by the European Patent Office Website Espacenet.com: Jeon Wan Ki; Vacuum Cleaner; Jun. 5, 2012 (Year: 2012).*

(Continued)

*Primary Examiner* — Kevin Joyner
(74) *Attorney, Agent, or Firm* — Fish & Richardson P.C.

(57) ABSTRACT

A cleaner station includes: a housing configured to receive a cleaner, a dust collecting motor that is accommodated in the housing and that is configured to generate a suction force for suctioning a foreign substance out of a dust bin of the cleaner, a dust storage module configured to, based on the dust collecting motor being operated, receive the foreign substance from the dust bin, and a sterilization module configured to sterilize the foreign substance received in the dust storage module. The dust storage module that (i) comprises a transmission panel configured to transmit sterilization light emitted by the sterilization module and (ii) is detachably coupled to the housing together with the transmission panel.

20 Claims, 19 Drawing Sheets

(56) References Cited

FOREIGN PATENT DOCUMENTS

| | | |
|---|---|---|
| KR | 2020007366 | 6/2020 |
| KR | 20200074054 | 6/2020 |

OTHER PUBLICATIONS

Office Action in Korean Appln. No. 10-2020-0108778, dated Oct. 6, 2022, 15 pages (with English translation).
International Search Report in International Appln. No. PCT/KR2021/011419, dated Dec. 17, 2021, 9 pages (with English translation).
Extended European Search Report in European Appln. No. 21862085.4, mailed on Oct. 9, 2024, 8 pages.

* cited by examiner

[FIG. 1]
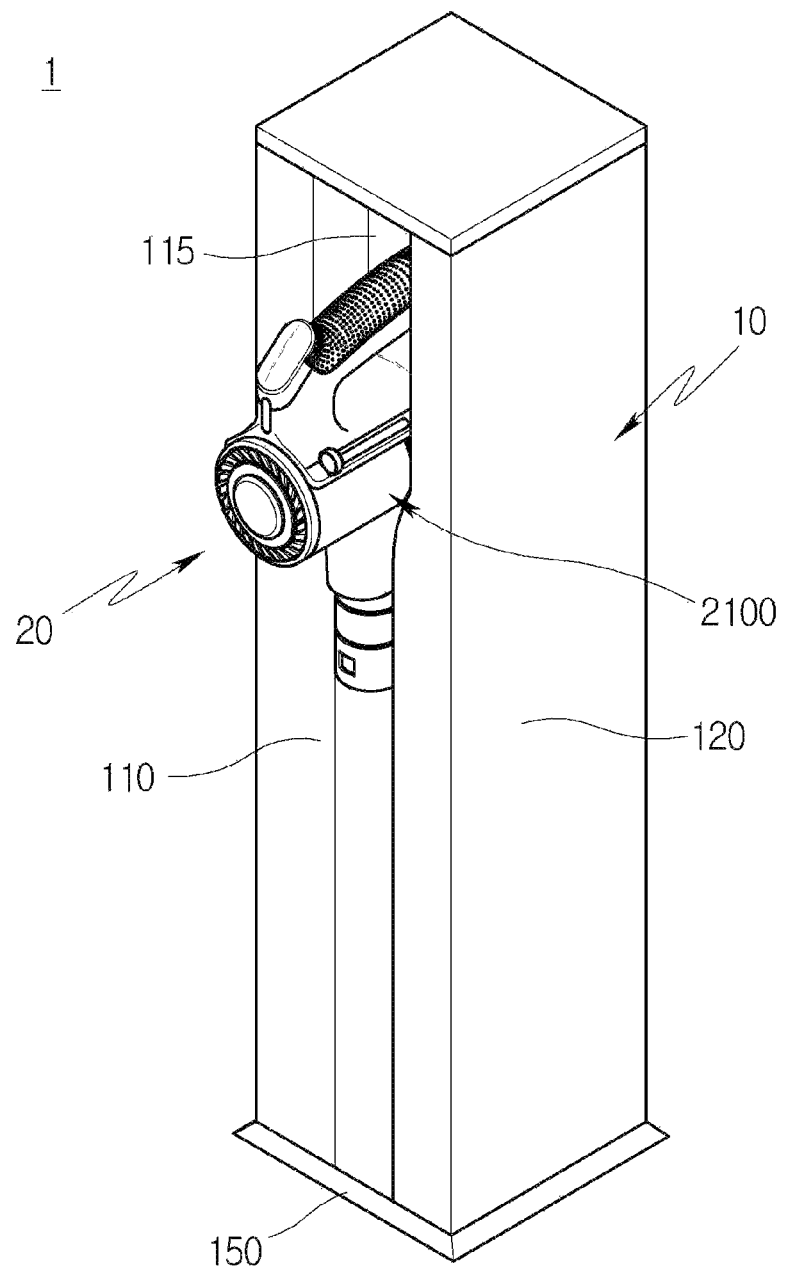

[FIG. 2]
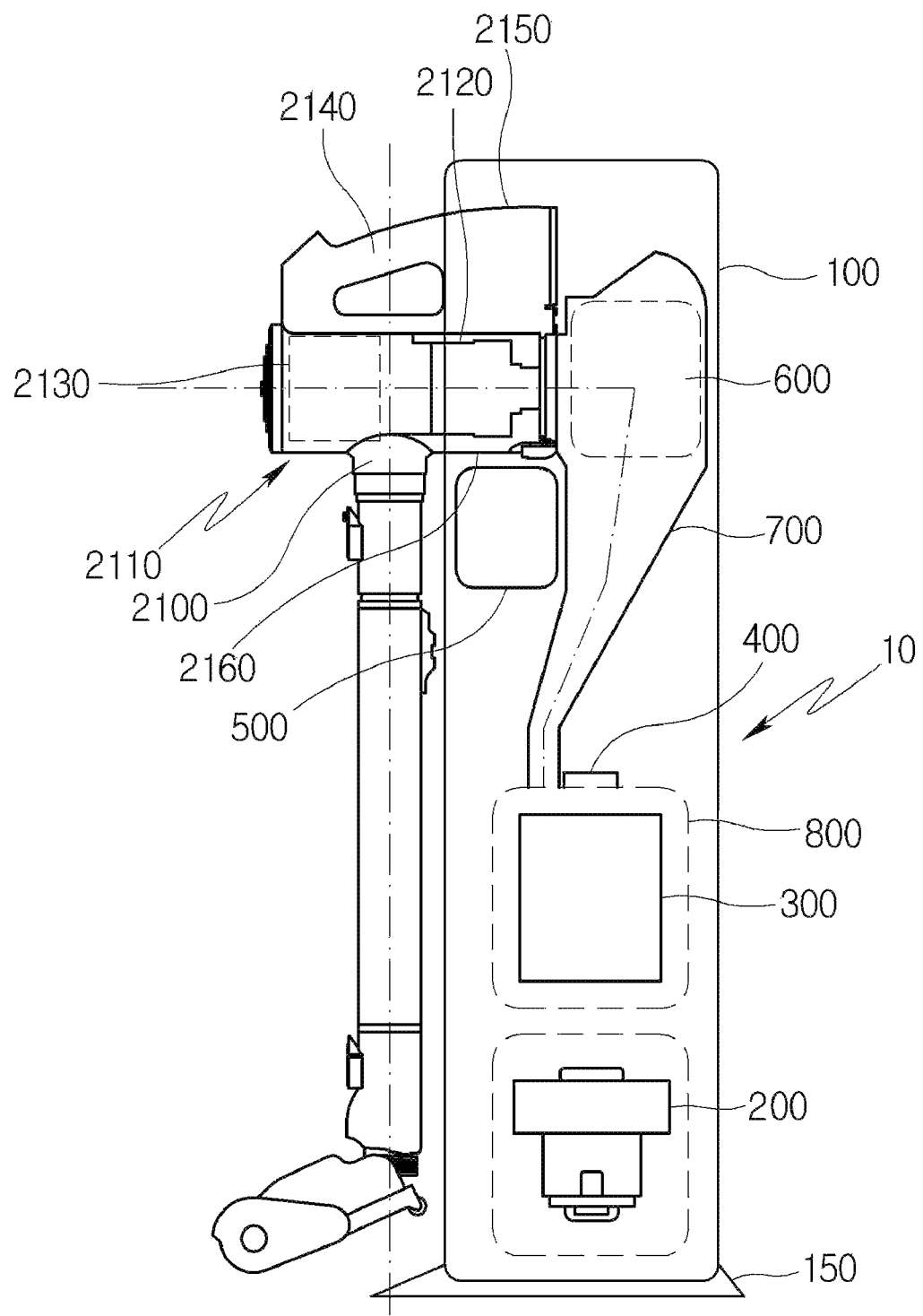

[FIG. 3]
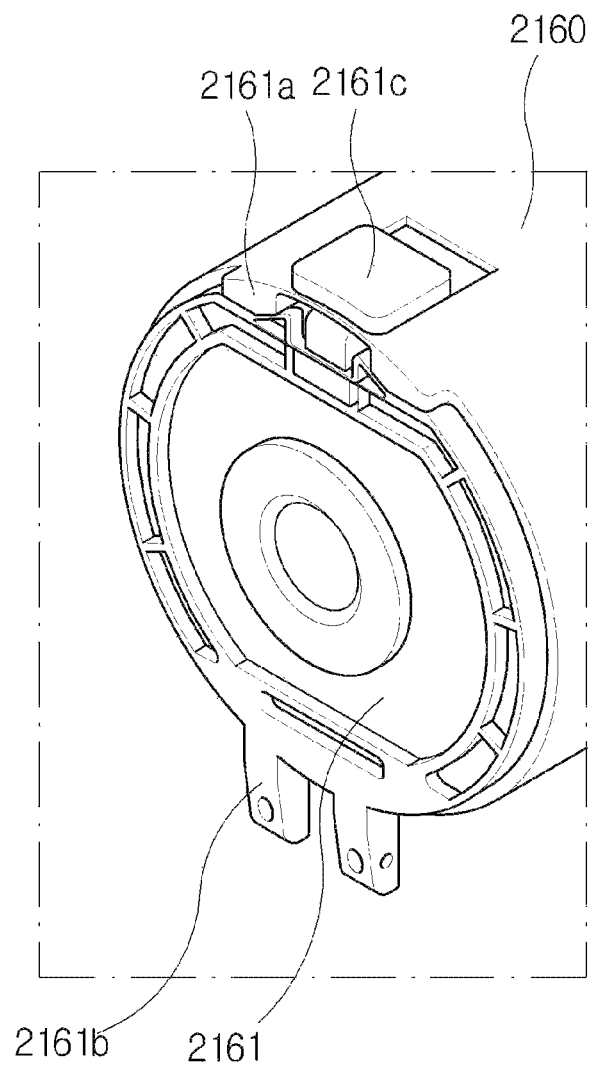

[FIG. 4]
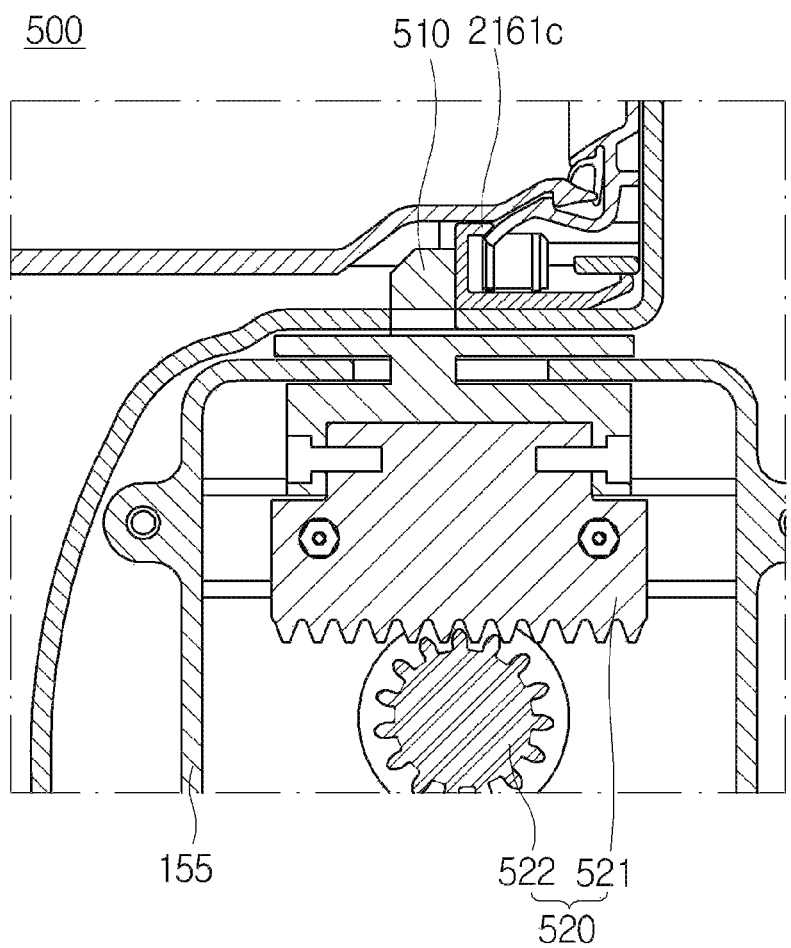

[FIG. 5]
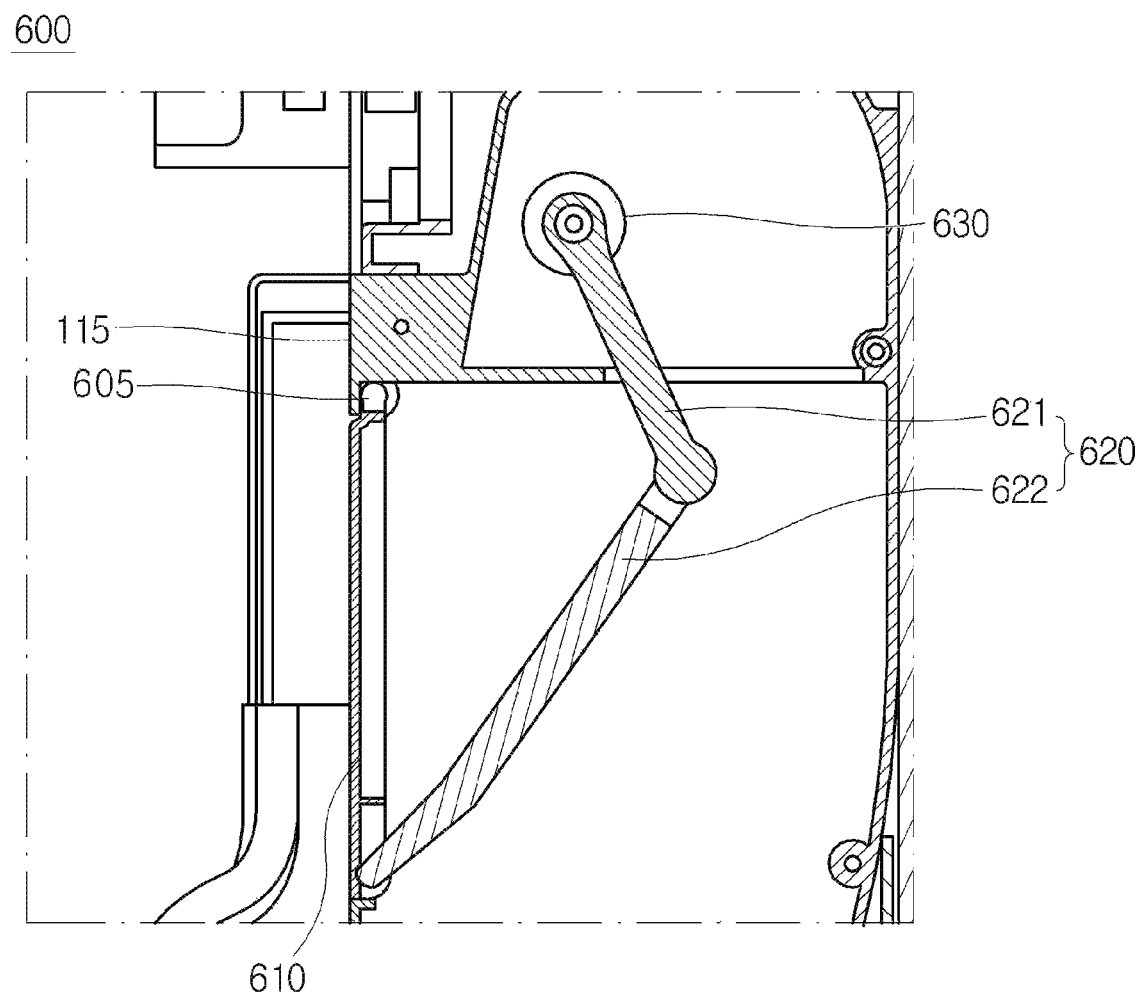

[FIG. 6]
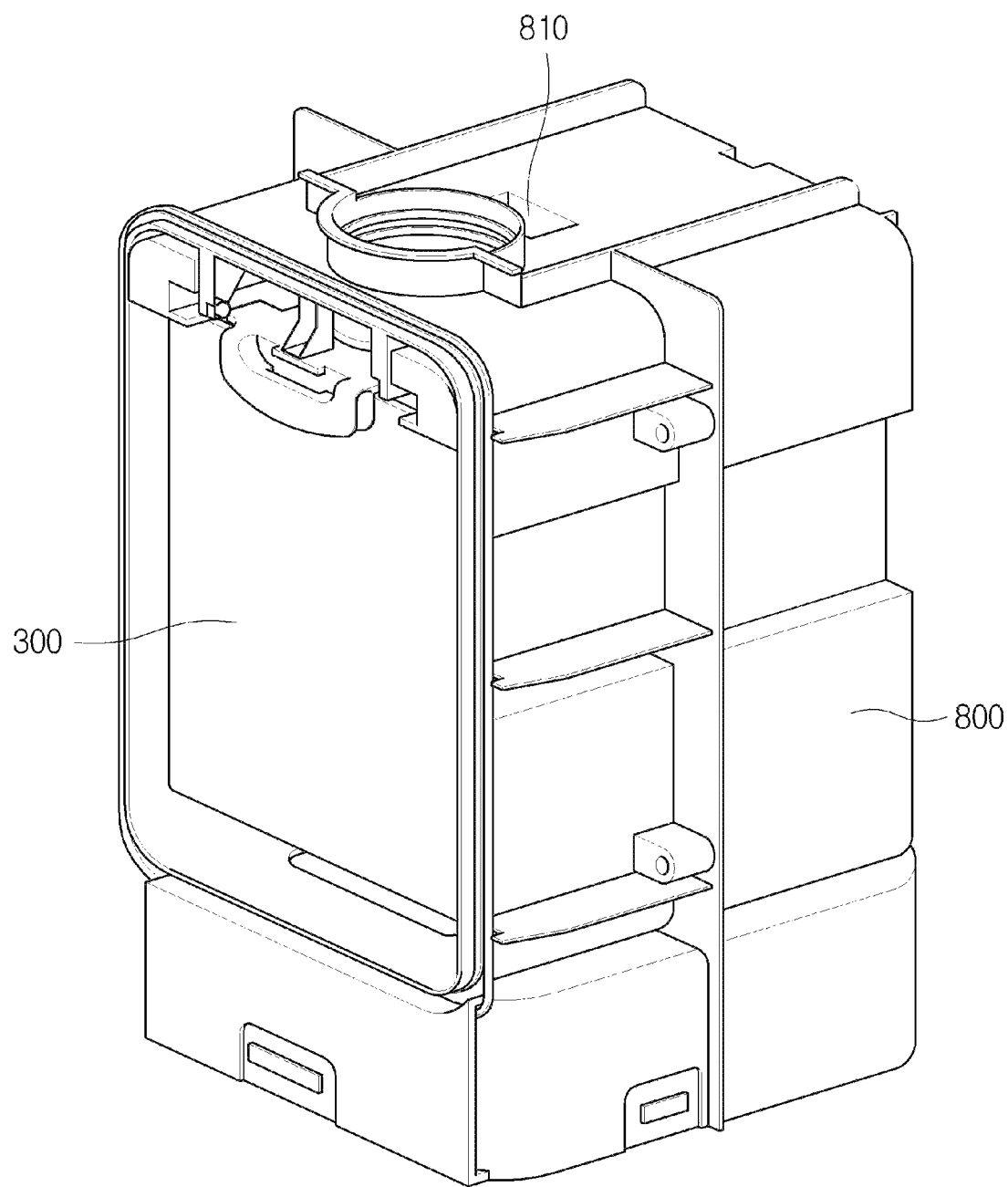

[FIG. 7]
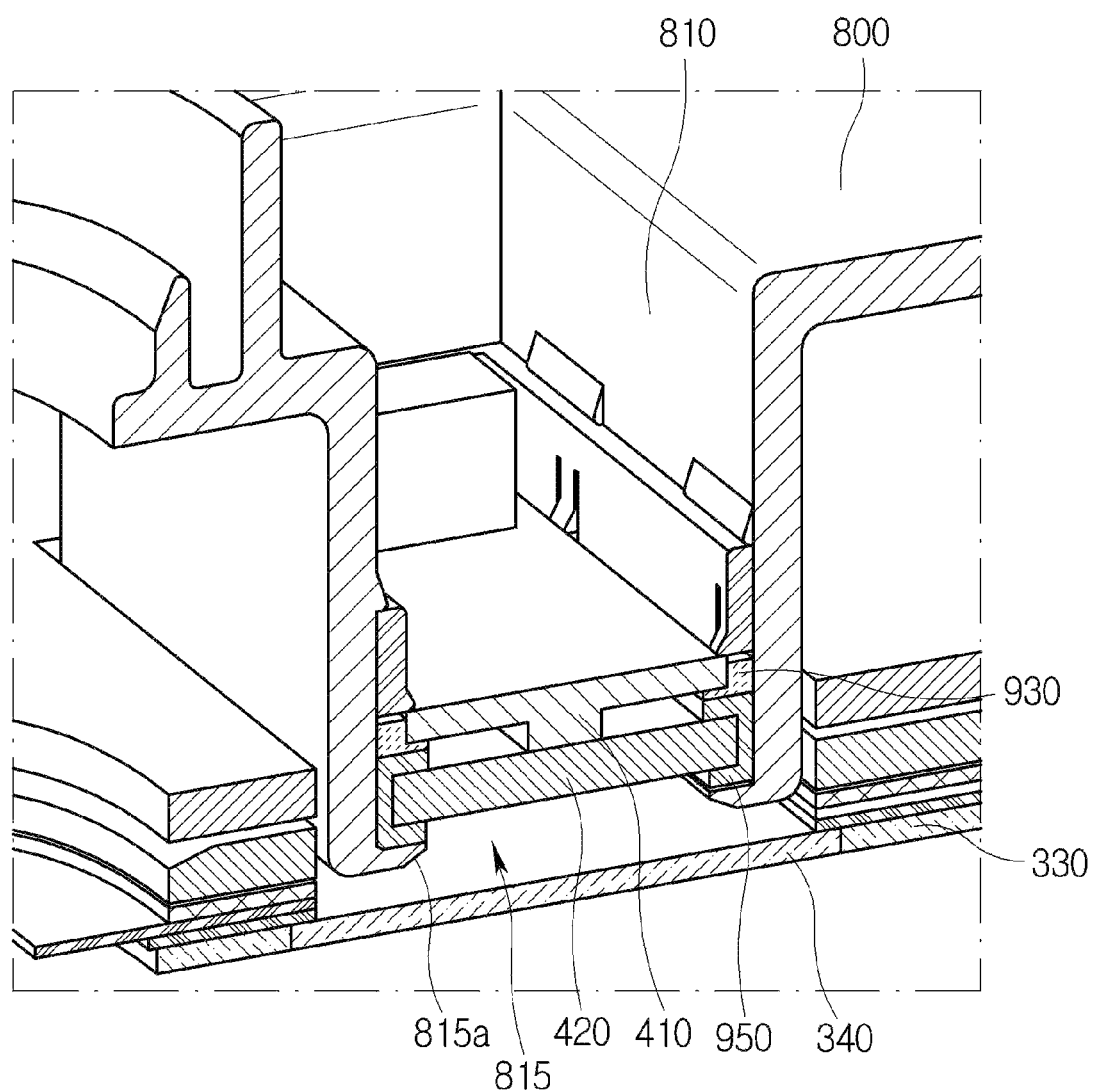

[FIG. 8]
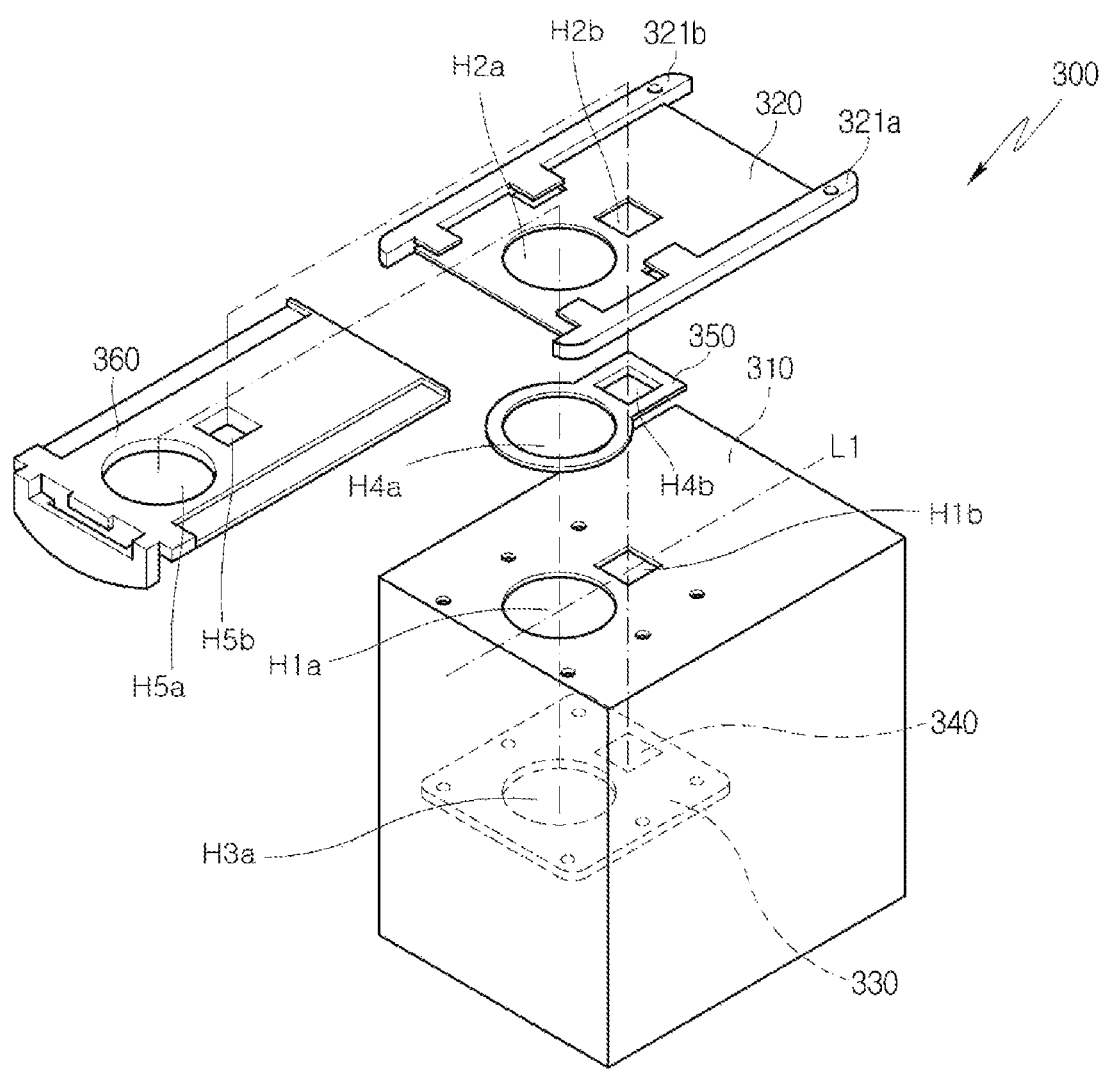

[FIG. 9]
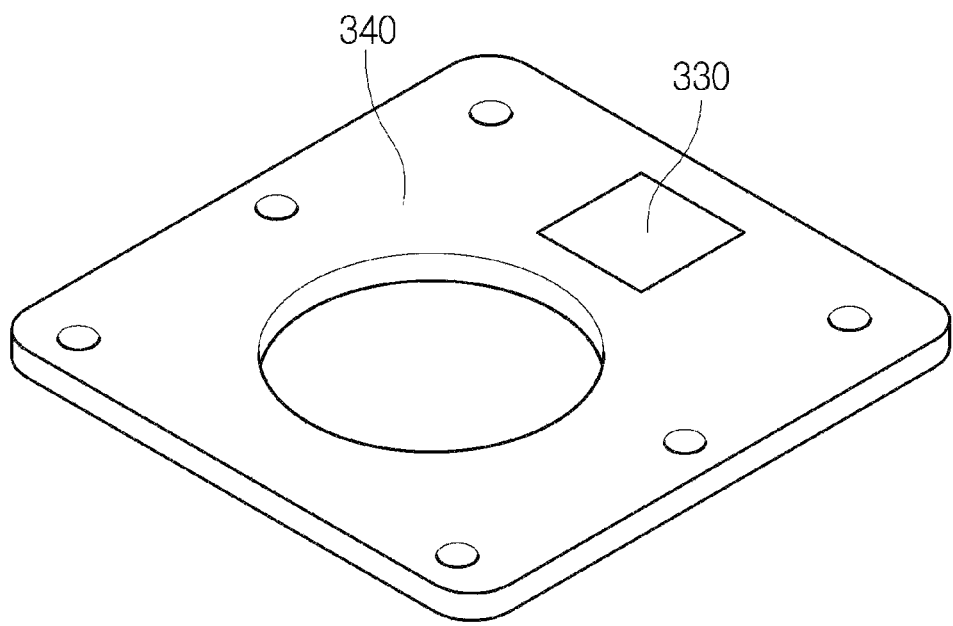

[FIG. 10]
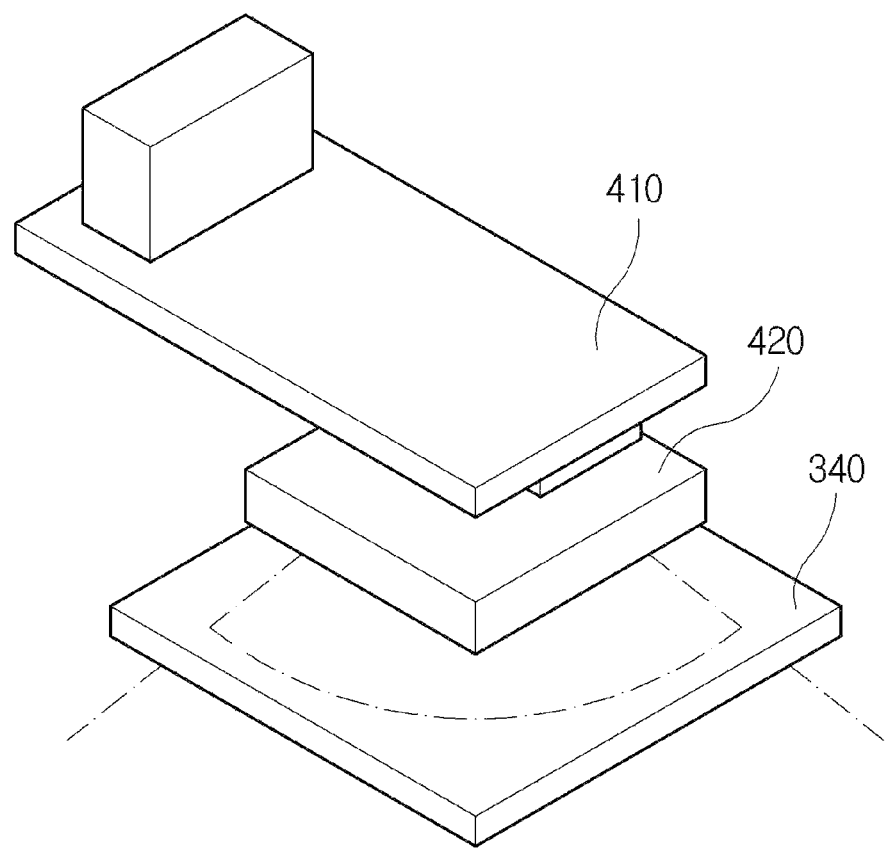

[FIG. 11A]
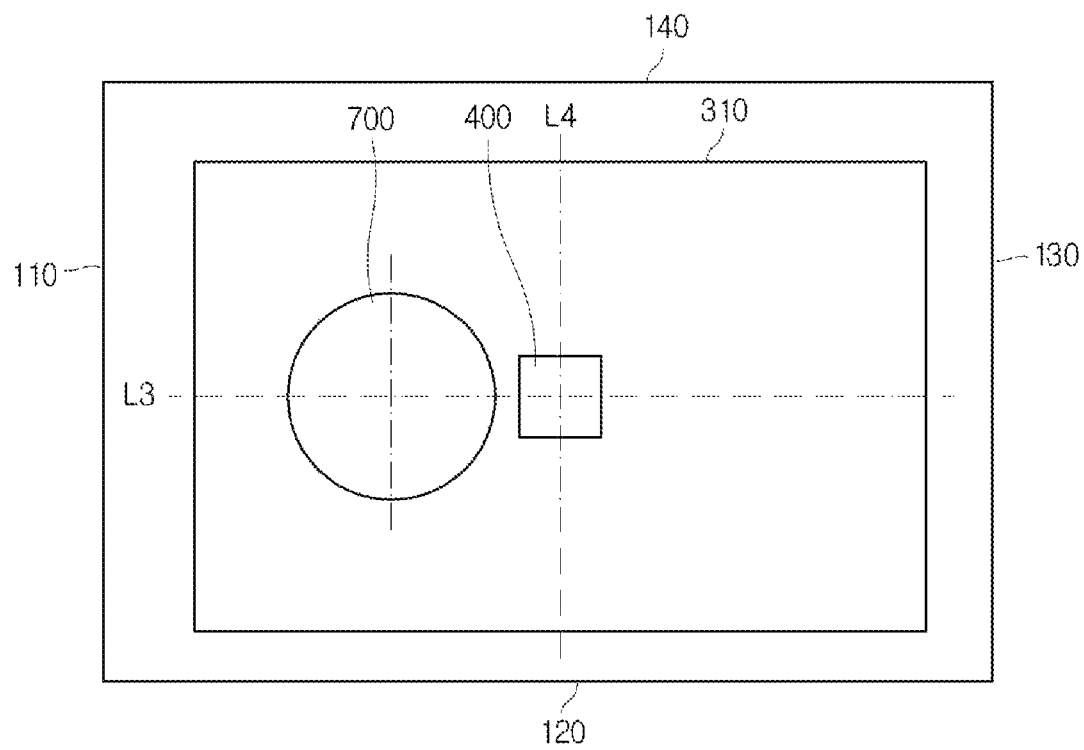

[FIG. 11B]
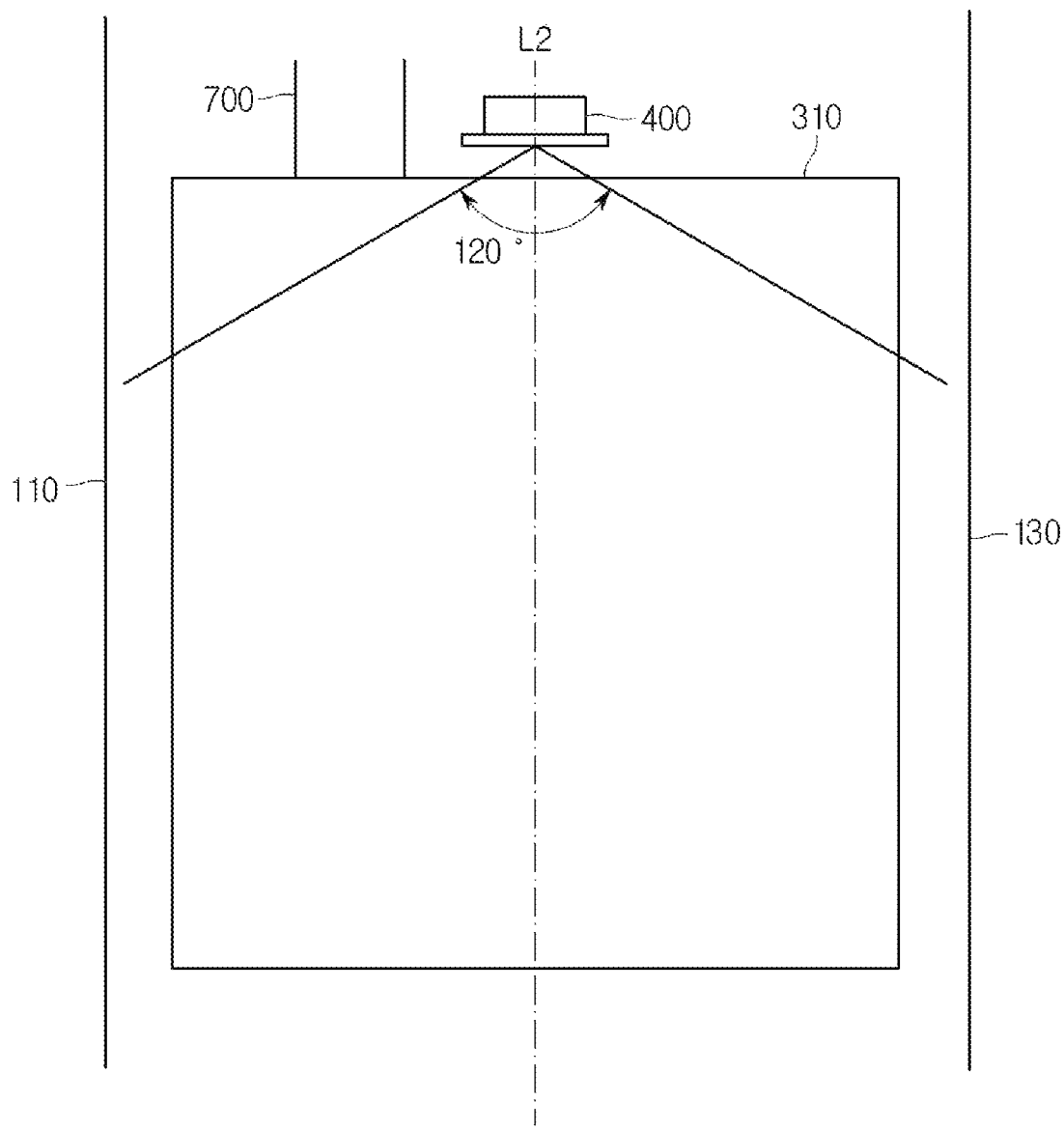

[FIG. 12A]
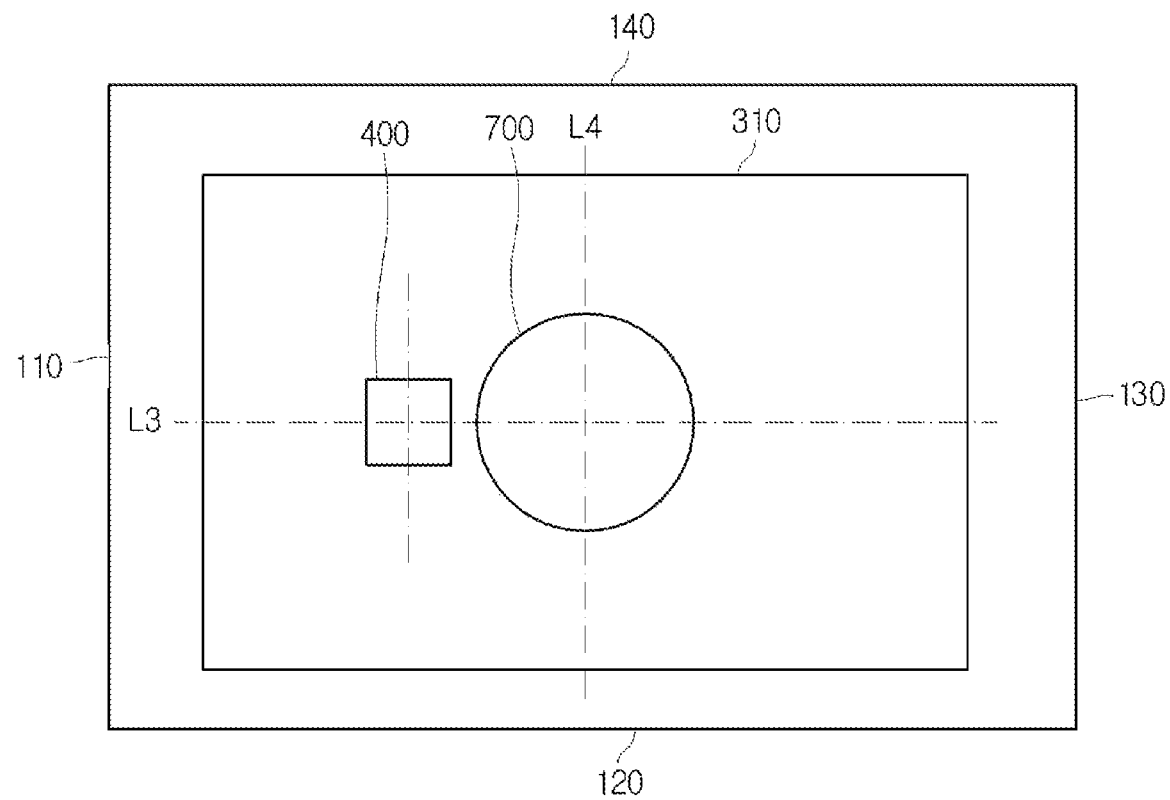

[FIG. 12B]
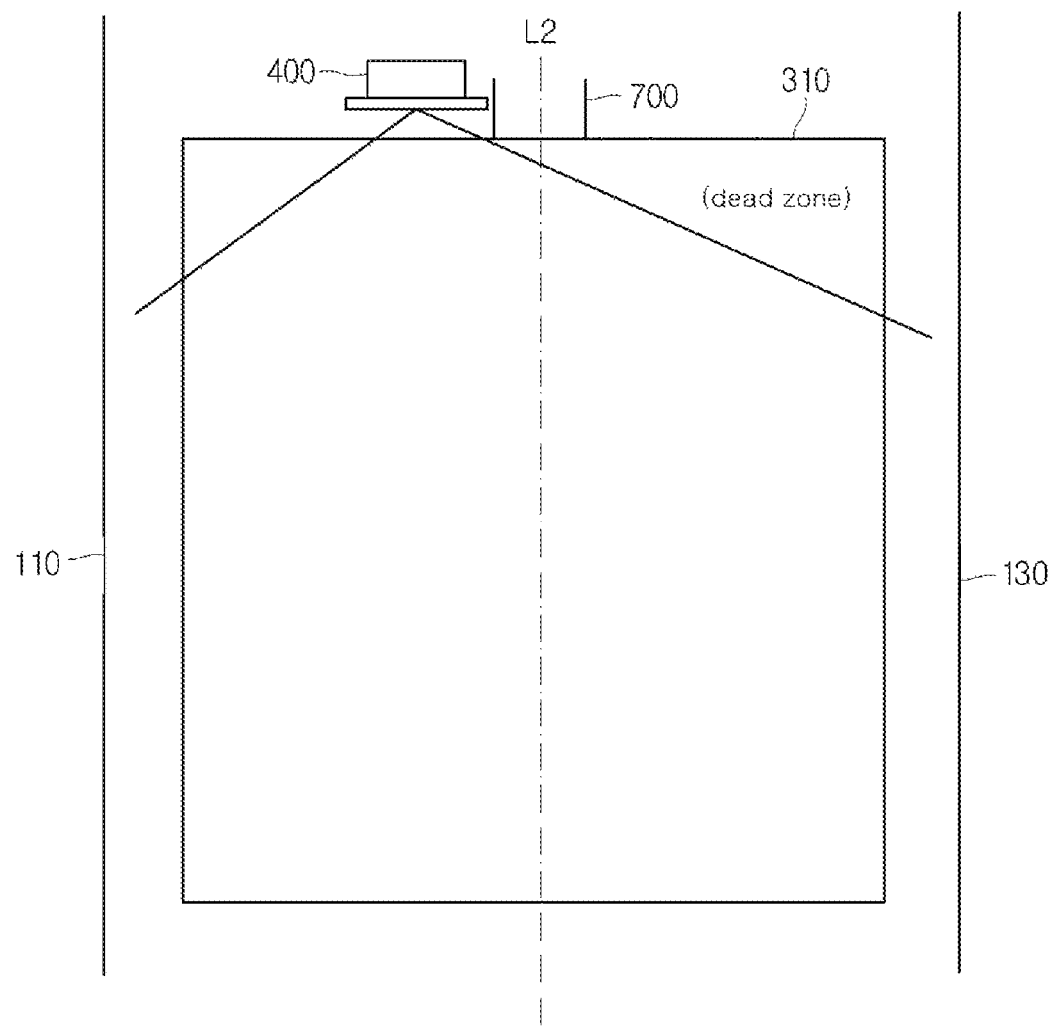

[FIG. 13A]
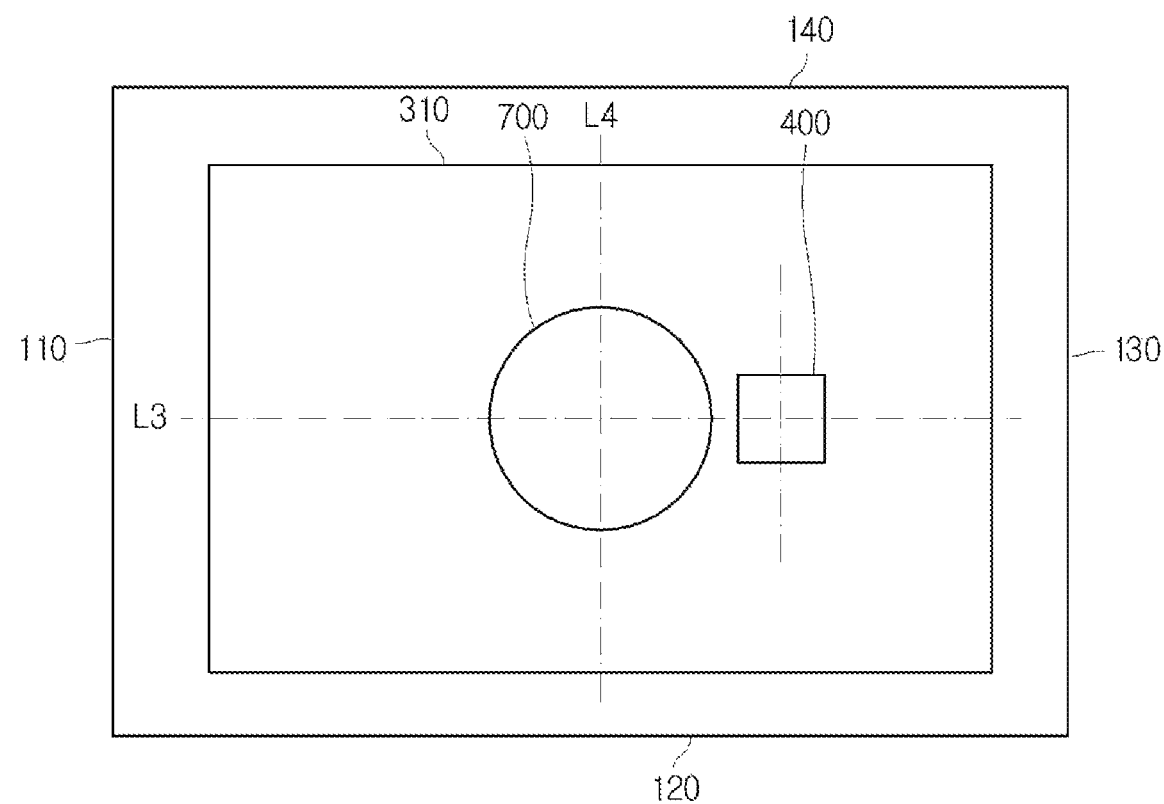

[FIG. 13B]
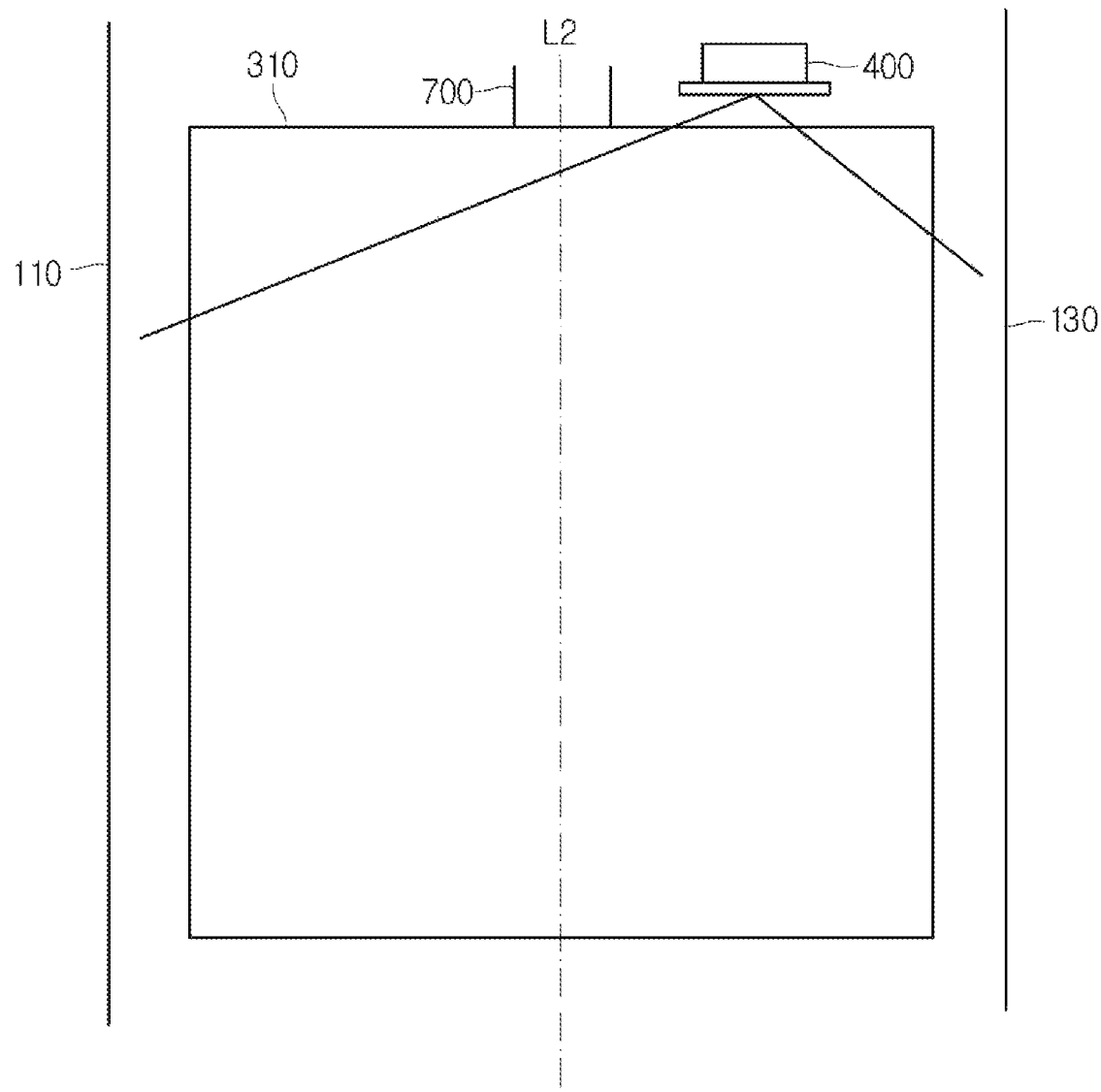

[FIG. 14A]
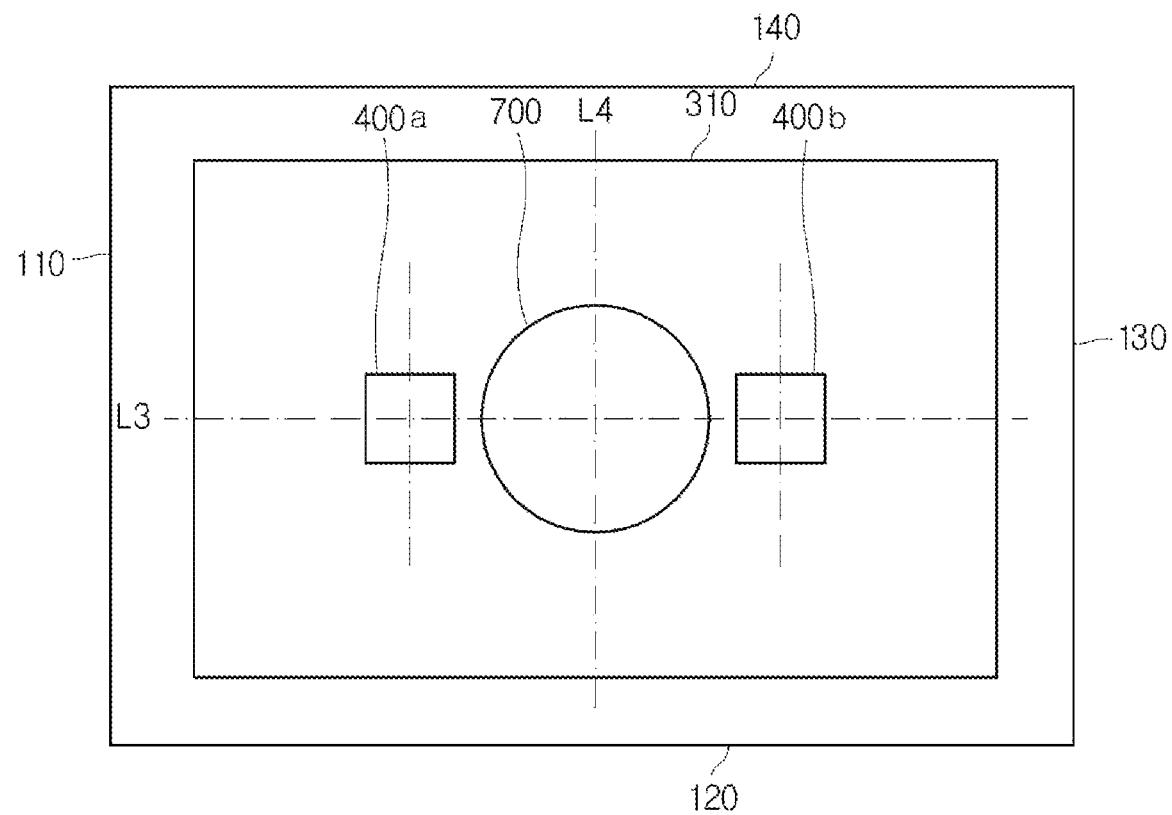

[FIG. 14B]
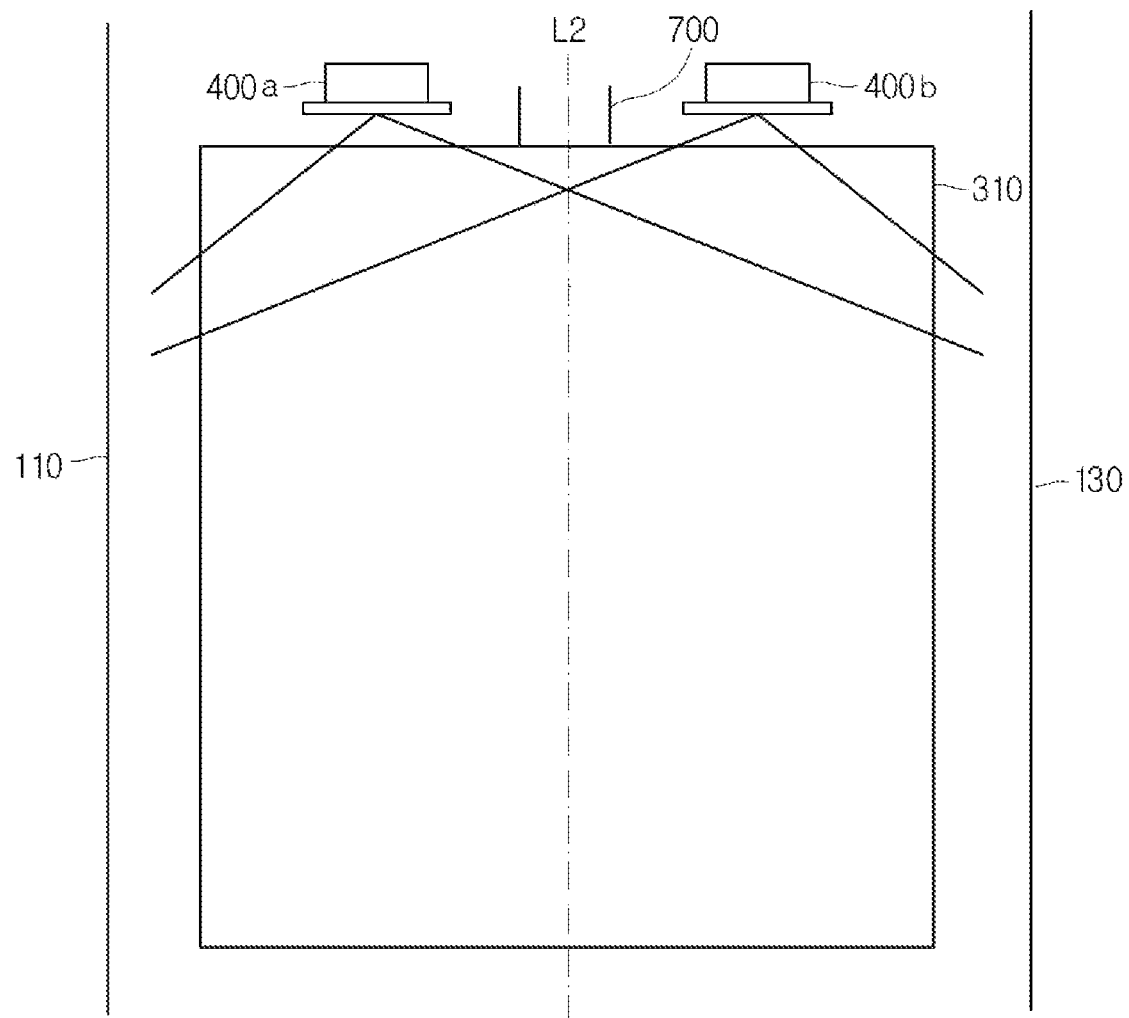

[FIG. 15]
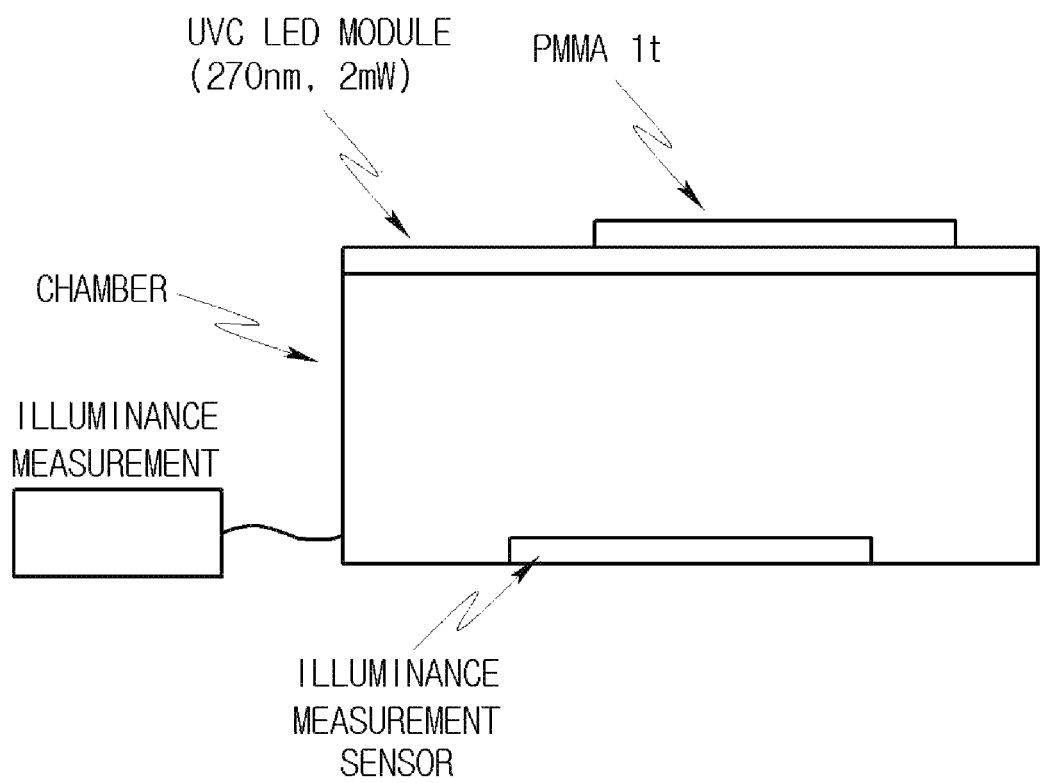

CLEANER STATION

CROSS REFERENCE TO RELATED APPLICATION

The present application claims priority to Korean Patent Application No. 10-2020-0108778, filed Aug. 27, 2020, the entire contents of which is incorporated herein for all purposes by this reference.

TECHNICAL FIELD

The present disclosure relates to a cleaner station configured to suck dust, stored in a cleaner, into the cleaner station, and more particularly, to a cleaner station capable of being managed in a hygienic environment by a sterilization module configured to sterilize the sucked dust.

BACKGROUND ART

In general, a cleaner refers to an electrical appliance that draws in small garbage or dust by sucking air using electricity and fills a dust bin provided in a product with the garbage or dust. Such a cleaner is generally called a vacuum cleaner.

The cleaners may be classified into a manual cleaner which is moved directly by a user to perform a cleaning operation, and an automatic cleaner which performs a cleaning operation while autonomously traveling. Depending on the shape of the cleaner, the manual cleaners may be classified into a canister cleaner, an upright cleaner, a handy cleaner, a stick cleaner, and the like.

The canister cleaners were widely used in the past as household cleaners. However, recently, there is an increasing tendency to use the handy cleaner and the stick cleaner in which a dust bin and a cleaner main body are integrally provided to improve convenience of use.

In the case of the canister cleaner, a main body and a suction port are connected by a rubber hose or pipe, and in some instances, the canister cleaner may be used in a state in which a brush is fitted into the suction port.

The handy cleaner has maximized portability and is light in weight. However, because the handy cleaner has a short length, there may be a limitation to a cleaning region. Therefore, the handy cleaner is used to clean a local place such as a desk, a sofa, or an interior of a vehicle. A user may use the stick cleaner while standing and thus may perform a cleaning operation without bending his/her waist. Therefore, the stick cleaner is advantageous for the user to clean a wide region while moving in the region. The handy cleaner may be used to clean a narrow space, whereas the stick cleaner may be used to clean a wide space and also used to a high place that the user's hand cannot reach. Recently, modularized stick cleaners are provided, such that types of cleaners are actively changed and used to clean various places.

However, because the stick cleaner has a dust bin with a small capacity for storing collected dust, which inconveniences the user because the user needs to empty the dust bin frequently.

As a document of the related art, Korean Patent Application Laid-Open No. 10-2020-0074001 discloses a cleaning apparatus including a vacuum cleaner and a docking station.

The cleaning apparatus disclosed in Korean Patent Application Laid-Open No. 10-2020-0074001 includes the vacuum cleaner including a dust collecting container for collecting foreign substances, and the docking station connected to the dust collecting container and configured to remove the foreign substances collected in the dust collecting container. The dust collecting container is configured to be docked to the docking station, and the docking station includes a suction device configured to suck foreign substances and inside air in the dust collecting container docked to the docking station.

In addition, Korean Patent Application Laid-Open No. 10-2020-0074001 includes a trapping part disposed in the docking station and configured to trap foreign substances.

However, the docking station disclosed in Korean Patent Application Laid-Open No. 10-2020-0074001 has a problem in that the foreign substances trapped by the trapping part are left unattended until a volume of the trapping part is filled with the foreign substances. Bacteria easily proliferate in the foreign substances left unattended over a long period of time in a dark internal space, and offensive odor may be created due to the proliferation of bacteria.

Therefore, the offensive odor is released to the outside when the suction device sucks the foreign substances and the inside air in the dust collecting container, which causes discomfort to a user.

In addition, there is a problem in that the inside of the docking station is contaminated by the proliferated bacteria.

Document of Related Art

Patent Document (Patent Document 1) Korean Patent Application Laid-Open No. 10-2020-0074001

DISCLOSURE

Technical Problem

An object of the present disclosure is to provide a cleaner station capable of hygienically managing a dust storage module that stores, for a long period of time, dust sucked from a dust bin of a cleaner.

Another object of the present disclosure is to provide a cleaner station capable of maintaining sterilization performance of a sterilization module that sterilizes a dust storage module without degrading the sterilization performance.

Still another object of the present disclosure is to provide a cleaner station capable of minimizing a dead zone which is a region that a range of sterilization light cannot reach.

Technical Solution

An embodiment of the present disclosure provides a cleaner station including: a housing coupled to a cleaner; a dust collecting motor accommodated in the housing and configured to generate a suction force for sucking dust in a dust bin of the cleaner; a dust storage module configured to collect the dust sucked from the inside of the dust bin by the dust collecting motor; and a sterilization module configured to sterilize the dust collected in the dust storage module, in which the dust storage module includes a transmission panel configured to transmit sterilization light emitted by the sterilization module and is detachably coupled in the housing together with the transmission panel.

In this case, the sterilization module may include: a light source configured to emit the sterilization light; and a protection panel disposed below the light source and configured to protect the light source.

In this case, the light source may be a UV-C LED.

A wavelength of the sterilization light emitted by the light source may be 405 nm.

Meanwhile, the cleaner station according to the embodiment of the present disclosure may further include a dust storage housing accommodated in the housing and having an internal space in which the dust storage module is coupled, the dust storage housing may have an accommodation groove formed by bending a part of an outer upper surface of the dust storage housing toward the internal space to accommodate the sterilization module, and a lower end of the accommodation groove may penetrate the internal space.

In addition, the dust storage module may further include: a dust bag having a volume that increases when the suction force is generated by the dust collecting motor to accommodate dust therein; an upper plate coupled to an outer upper surface of the dust bag and configured to be inserted into the dust storage housing in a sliding manner; and a lower plate coupled to the transmission panel and coupled to an inner upper surface of the dust bag.

Meanwhile, the sterilization module and the transmission panel may be disposed to face each other when the upper plate is inserted into and coupled to the dust storage housing.

Another embodiment of the present disclosure provides a cleaner station including: a housing coupled to a cleaner; a dust collecting motor accommodated in the housing and configured to generate a suction force for sucking dust in a dust bin of the cleaner; a dust storage module configured to collect the dust sucked from the inside of the dust bin by the dust collecting motor; a dust storage housing accommodated in the housing and having an internal space in which the dust storage module is coupled; and a sterilization module configured to sterilize the dust collected in the dust storage module, in which the dust storage module includes a dust bag having a volume that increases when the suction force is generated by the dust collecting motor to accommodate dust therein, in which the sterilization module is disposed above the dust storage housing and includes a light source configured to emit sterilization light, and in which an imaginary connection line connecting a center of an upper surface of the dust bag and a center of a lower surface of the dust bag passes through an approximate center of the light source.

In this case, the sterilization module may include a protection panel disposed below the light source and configured to protect the light source.

In addition, the dust storage module may further include: a transmission panel configured to transmit the sterilization light emitted from the sterilization module; an upper plate coupled to an outer upper surface of the dust bag and configured to be inserted into the dust storage housing in a sliding manner; and a lower plate coupled to the transmission panel and coupled to an inner upper surface of the dust bag.

In this case, an area of the transmission panel may be larger than an area of the protection panel.

In this case, the light source may be a UV-C LED.

Alternatively, as an example, a wavelength of the sterilization light emitted by the light source may be 405 nm.

Meanwhile, the dust storage housing may have an accommodation groove formed by bending a part of an outer upper surface of the dust storage housing toward the internal space to accommodate the sterilization module, and a lower end of the accommodation groove may penetrate the internal space.

In addition, the sterilization module and the transmission panel may be disposed to face each other when the upper plate is inserted into and coupled to the dust storage housing.

Advantageous Effect

The cleaner station according to the present disclosure has the sterilization module that may sterilize the dust storage module to prevent the proliferation of bacteria in the dust storage module, thereby hygienically managing the dust storage module.

In addition, according to the cleaner station according to the present disclosure, the dust storage module is detachably coupled in the cleaner station, the transmission panel, which transmits the sterilization light, is coupled to the dust storage module, and the transmission panel is provided as a replaceable consumable component. There is concern that dust may be attached to the transmission panel during the suction process, which may degrade transmission efficiency. However, since the transmission panel is consistently replaced, it is possible to maintain the performance of the sterilization module for sterilizing the dust storage module without degrading the performance.

In addition, according to the cleaner station according to the present disclosure, the imaginary connection line, which connects the center of the upper surface of the dust bag and the center of the lower surface of the dust bag, passes through the approximate center of the light source that emits the sterilization light. Therefore, it is possible to minimize the dead zone which is a region that a range of the sterilization light cannot reach.

DESCRIPTION OF DRAWINGS

FIG. 1 is a perspective view illustrating a dust removing system including a cleaner station and a cleaner according to an embodiment of the present disclosure.

FIG. 2 is a view illustrating a state in which the cleaner is coupled to the cleaner station and an interior of the cleaner station at a lateral side of the cleaner station.

FIG. 3 is an enlarged view illustrating a structure for opening or closing a dust bin of the cleaner.

FIG. 4 is an enlarged view of a cover opening unit of the cleaner station.

FIG. 5 is an enlarged view of a door unit of the cleaner station.

FIG. 6 is a view illustrating a state in which a dust storage module is accommodated in and coupled to a dust storage housing.

FIG. 7 is an enlarged view of an accommodation groove provided in the dust storage housing.

FIG. 8 is an exploded perspective view of the dust storage module.

FIG. 9 is a view illustrating a state in which a transmission panel is coupled to a lower plate.

FIG. 10 is a view illustrating a configuration of a sterilization module and a state in which sterilization light is emitted from the sterilization module.

FIGS. 11A and 11B are schematic views illustrating an arrangement relationship between a suction flow path and a sterilization module in the cleaner station according to the embodiment of the present disclosure.

FIGS. 12A to 14B are views illustrating various embodiments of the arrangement relationship between the suction flow path and the sterilization module.

FIG. 15 is a view illustrating an experimental device used to measure the transmittance of the sterilization light of the transmission panel 340 made of PMMA.

MODE FOR INVENTION

Hereinafter, exemplary embodiments of the present disclosure will be described in detail with reference to the accompanying drawings.

The present disclosure may be variously modified and may have various embodiments, and particular embodiments illustrated in the drawings will be specifically described below. The description of the embodiments is not intended to limit the present disclosure to the particular embodiments, but it should be interpreted that the present disclosure is to cover all modifications, equivalents and alternatives falling within the spirit and technical scope of the present disclosure.

In the description of the present disclosure, the terms such as "first" and "second" may be used to describe various constituent elements, but the constituent elements may not be limited by the terms. These terms are used only to distinguish one constituent element from another constituent element. For example, a first component may be named a second component, and similarly, the second component may also be named the first component, without departing from the scope of the present disclosure.

The term "and/or" may include any and all combinations of a plurality of the related and listed items.

When one constituent element is described as being "coupled" or "connected" to another constituent element, it should be understood that one constituent element can be coupled or connected directly to another constituent element, and an intervening constituent element can also be present between the constituent elements. When one constituent element is described as being "coupled directly to" or "connected directly to" another constituent element, it should be understood that no intervening constituent element is present between the constituent elements.

The terminology used herein is used for the purpose of describing particular embodiments only and is not intended to limit the present disclosure. Singular expressions may include plural expressions unless clearly described as different meanings in the context.

The terms "comprises," "comprising," "includes," "including," "containing," "has," "having" or other variations thereof are inclusive and therefore specify the presence of stated features, integers, steps, operations, elements, and/or components, but do not preclude the presence or addition of one or more other features, integers, steps, operations, elements, components, and/or groups thereof.

Unless otherwise defined, all terms used herein, including technical or scientific terms, may have the same meaning as commonly understood by those skilled in the art to which the present disclosure pertains. The terms such as those defined in a commonly used dictionary may be interpreted as having meanings consistent with meanings in the context of related technologies and may not be interpreted as ideal or excessively formal meanings unless explicitly defined in the present application.

Further, the following embodiments are provided to more completely explain the present disclosure to those skilled in the art, and shapes and sizes of elements illustrated in the drawings may be exaggerated for a more apparent description.

FIG. 1 is a perspective view illustrating a dust removing system 1 including a cleaner station 10 and a cleaner 20 according to an embodiment of the present disclosure, FIG. 2 is a view illustrating a state in which the cleaner 20 is coupled to the cleaner station 10 and an interior of the cleaner station 10 at a lateral side of the cleaner station 10, FIG. 3 is an enlarged view of a structure for opening or closing a dust bin 2160 of the cleaner 20, FIG. 4 is an enlarged view of a cover opening unit 500 of the cleaner station 10, and FIG. 5 is an enlarged view of the door unit 600 of the cleaner station 10.

Referring to FIGS. 1 to 5, the dust removing system 1 may include the cleaner station 10 and the cleaner 20.

The cleaner 20 may be coupled to a front side of the cleaner station 10. More specifically, a cleaner main body 2100 of the cleaner 20 may be coupled to the front side of the cleaner station 10.

In this case, the front side of the cleaner station 10 may be defined as a side in direction in which a coupling part 115, which is recessed from a housing 100 to be described below so as to have a shape corresponding to the main body 2100 of the cleaner 20, is directed. A side, which is opposite to the housing 100 based on the coupling part 115, may be defined as a rear side.

First, a configuration of the cleaner main body 2100 of the cleaner 20, which is configured to be coupled to the cleaner station 10 according to the embodiment of the present disclosure, will be briefly described.

Referring to FIG. 2, the cleaner main body 2100 may include a suction part 2110 configured to provide a flow path through which air containing dust may flow, a dust separating part 2120 configured to communicate with the suction part 2110 and separate the dust sucked into the dust separating part 2120 through the suction part 2110, a suction motor 2130 configured to generate a suction force for sucking the air, a handle 2140 configured to be grasped by a user, and a battery housing 2150 configured to accommodate a battery therein.

In addition, the cleaner main body 2100 may further include the dust bin 2160.

In this case, the dust bin 2160 may communicate with the dust separating part 2120 and store the dust separated by the dust separating part 2120.

Referring to FIG. 3, the dust bin 2160 may include a discharge cover 2161. The discharge cover 2161 may include a cover main body 2161a and a hinge part 2161b. The cover main body 2161a may be rotated about the hinge part 2161b to open or close the dust bin 2160. The hinge part 2161b may be disposed adjacent to the battery housing 2150. The discharge cover 2161 may be coupled to the dust bin 2160 by a hook engagement.

Meanwhile, the dust bin 2160 may further include a coupling lever 2161c. The discharge cover 2161 may be separated from the dust bin 2160 by means of the coupling lever 2161c. The coupling lever 2161c may be disposed downward based on the state in which the cleaner 20 is coupled to the cleaner station 10. When an external force is applied to the coupling lever 2161c, the coupling lever 2161c may elastically deform a hook extending from the cover main body 2161a to release the hook engagement between the cover main body 2161a and the dust bin 2160.

Meanwhile, the 'coupling' between the cleaner 20 and the cleaner station 10, which will be repeatedly mentioned throughout the present specification, will be described in detail. In this case, the coupling is a concept including physical coupling, electrical coupling, and fluidic coupling.

Specifically, the physical coupling may refer to the connection in the state in which the cleaner 20 is seated on the coupling part 115 by the user and fixed and/or sealed in the cleaner station 10 by a mechanical component provided in the cleaner station 10 to enable the fluid coupling to be described below.

In addition, the electrical coupling may refer to the connection in the state in which the battery of the cleaner 20 comes into contact with a separate charging part provided in the cleaner station 10 and the cleaner 20 may be supplied with electric power from the cleaner station 10 or the connection between the cleaner 20 and the cleaner station 10 in the state in which the physical coupling may be detected by various types of sensors provided in the cleaner station 10.

In addition, the fluidic coupling may refer to a state in which a door 610 of the cleaner station 10, which will be described below, is opened, and the discharge cover 2161 of the cleaner 20 is also opened, such that the dust bin 2160 of the cleaner 20 communicates with a suction flow path 700 of the cleaner station 10. The fluidic coupling is implemented after the physical coupling and/or the electrical coupling is implemented. In the state in which the fluidic coupling is implemented, the air, together with the dust, in the dust bin 2160 of the cleaner 20 may pass through the suction flow path 700 and move to a dust bag 310 to be described below.

Next, the cleaner station 10 according to the embodiment of the present disclosure will be described.

Referring to FIG. 2, the cleaner station 10 may include the housing 100, a dust collecting motor 200, a dust storage module 300, and a sterilization module 400.

The housing 100 is a component to which the cleaner 20 is coupled. The housing 100 may define an external appearance of the cleaner station 10. Specifically, the housing 100 may be provided in the form of a column including one or more outer wall surfaces. For example, the housing 100 may be formed in a shape similar to a quadrangular column.

The housing 100 has therein a space that may accommodate the dust collecting motor 200, the dust storage module 300, and the sterilization module 400.

The housing 100 may include a floor support part 150. In this case, the floor support part 150 may be disposed toward the floor. A bottom surface of the floor support part 150, which is in contact with the floor, may be disposed in parallel with the floor. Of course, the bottom surface of the floor support part 150 may be disposed to be inclined with respect to the floor at a predetermined angle. The above-mentioned configuration may be advantageous in stably supporting the dust collecting motor 200 accommodated in the housing 100 and maintaining balance of an overall weight even in a case in which the cleaner 20 is coupled.

In addition, the floor support part 150 may be provided in the form of a plate extending from the bottom surface of the housing 100 to increase an area being in contact with the floor in order to prevent the cleaner station 10 from falling down and maintain the balance.

As described above, the housing 100 may include one or more outer wall surfaces. For example, the housing 100 may include a first outer wall surface 110 on which the coupling part 115 is provided. The housing 100 may further include a second outer wall surface 120, a third outer wall surface 130, and a fourth outer wall surface 140 sequentially disposed counterclockwise when viewed from the first outer wall surface 110.

The coupling part 115 provided on the first outer wall surface 110 may be made as the first outer wall surface 110 is recessed to correspond to a shape of a part of the cleaner 20 on which the dust bin 2160 is disposed. With this configuration, a part of the cleaner 20 may be coupled to the cleaner station 10 and supported by the cleaner station 10.

The housing 100 may be opened such that some of the components (e.g., the dust storage module 300) accommodated in the housing 100 are exposed. For example, when the cleaner station 10 is viewed from the front side, a part of a left side of the first outer wall surface 110 may be opened toward the fourth outer wall surface 140, and a part of a right side of the first outer wall surface 110 may be opened toward the second outer wall surface 120.

Alternatively, as another example, a part of the first outer wall surface 110 and a part of the second outer wall surface 120 may be integrated and opened together toward the second outer wall surface 120. Alternatively, a part of the first outer wall surface 110 and a part of the fourth outer wall surface 140 may be integrated and opened together toward the fourth outer wall surface 140.

The cleaner station 10 according to the embodiment of the present disclosure may further include the cover opening unit 500.

Referring to FIG. 4, the cover opening unit 500 may be configured to open the discharge cover 2161 of the cleaner 20.

The cover opening unit 500 may include a push protrusion 510, cover opening gears 520, and a cover opening motor (not illustrated).

When the cleaner 20 is coupled, the push protrusion 510 may be disposed at a position at which the push protrusion 510 may push the coupling lever 2161c. The push protrusion 510 may rectilinearly reciprocate to press the coupling lever 2161c. Specifically, the push protrusion 510 may be coupled to the cover opening gears 520 and moved together with the cover opening gears 520 by the movements of the cover opening gears 520.

The cover opening motor may provide the cover opening gears 520 with power for moving the push protrusion 510.

The cover opening gears 520 may be coupled to the cover opening motor and may move the push protrusion 510 using the power from the cover opening motor. More specifically, the cover opening gears 520 may include a first cover opening gear 521 configured to receive rotational power from a shaft of the cover opening motor, and a second cover opening gear 522 engaging with the first cover opening gear 521 and configured to transmit a rectilinear reciprocating motion to the push protrusion 510.

In this case, the first cover opening gear 521 may be a pinion gear, and the second cover opening gear 522 may be a rack gear.

In other words, when the main body 2100 of the cleaner 20 is fixed to the coupling part 115, the cover opening motor may separate the discharge cover 2161 from the dust bin 2160 by moving the push protrusion 510 using the cover opening gears 520.

The cleaner station 10 according to the embodiment of the present disclosure may further include the door unit 600.

Referring to FIG. 5, the door unit 600 may include a door 610, a door arm 620, and a door motor 630.

The door 610 may be coupled to the coupling part 115 by means of a hinge 605 and rotated about the hinge 605 to allow the inside and the outside of the housing 100 to communicate with each other.

More specifically, when the door arm 620 pulls the door 610 in the state in which the door 610 closes the inside of the housing 100, the door 610 may rotate toward the inside of the housing 100 of the cleaner station 10. Meanwhile, when the door arm 620 pushes the door, the door 610 may rotate toward the outside of the cleaner station 10.

The door motor 630 may provide the door arm 620 with power for rotating the door 610. Specifically, the door motor 630 may rotate the door arm 620 in a forward direction or a reverse direction. In this case, the forward direction may mean a direction in which the door arm 620 pulls the door 610 toward the inside of the housing 100. In addition, the reverse direction may mean a direction in which the door arm 620 pushes the door 610 toward the outside of the housing 100.

The door arm 620 may connect the door 610 and the door motor 630 and open or close the door 610 using the power generated from the door motor 630.

For example, the door arm 620 may include a first door arm 621 and a second door arm 622. One end of the first door arm 621 may be coupled to the door motor 630. The first door arm 621 may be rotated by the power of the door motor 630. The other end of the first door arm 621 may be rotatably coupled to the second door arm 622. The first door arm 621 may transmit a force transmitted from the door motor 630 to the second door arm 622. One end of the second door arm 622 may be coupled to the first door arm 621. The other end of the second door arm 622 may be coupled to the door 610. The second door arm 622 may push or pull the door 610.

The cleaner station 10 according to the embodiment of the present disclosure may further include the suction flow path 700.

In this case, the suction flow path 700 is a passageway through which air containing dust may flow. Therefore, when the discharge cover 2161 is separated from the dust bin 2160, the dust in the dust bin 2160 may be captured into the dust storage module 300 through the suction flow path 700.

Meanwhile, the dust collecting motor 200 may be accommodated in the housing 100 may be disposed below the dust storage module 300. The dust collecting motor 200 may provide a suction force to the suction flow path 700. Therefore, the dust collecting motor 700 may suck the dust in the dust bin 2160 of the cleaner 20.

Next, the dust storage module 300 is accommodated in the housing 100 and collects the dust sucked into the dust bin 2160 of the cleaner 20 by the dust collecting motor 200.

The dust storage module 300 may be detachably coupled to the housing 100.

Therefore, when the housing 100 is opened, the dust storage module 300 may be separated from the housing 100 and discarded, and a new dust storage module 300 may be coupled to the housing 100. That is, the dust storage module 300 may be defined as a consumable component.

FIG. 6 is a view illustrating a state in which the dust storage module 300 is accommodated in and coupled to a dust storage housing 800, and FIG. 7 is an enlarged view of an accommodation groove 810 provided in the dust storage housing 800.

Referring to FIGS. 6 and 7, the cleaner station 10 according to the embodiment of the present disclosure may further include the dust storage housing 800 accommodated in the housing 100 and having an internal space in which the dust storage module 300 is coupled.

The dust storage housing 800 may have the accommodation groove 810 that accommodates the sterilization module 400.

A detailed configuration of the sterilization module 400 accommodated in the accommodation groove 810 will be described below. First, the accommodation groove 810 will be described. The accommodation groove 810 may be made by bending a part of an outer upper surface of the dust storage housing 800 toward the internal space of the dust storage housing 800. In addition, an opening portion 815 may be provided at a lower end of the accommodation groove 810, and the opening portion 815 may be penetratively formed toward an internal space of the dust storage housing 800 to transmit sterilization light emitted from the sterilization module 400.

An inclined surface 815a may be provided at an edge of the opening portion 815 in such a manner that an area of an opened region of the opening portion 815 increases downward. This configuration may prevent a part of the accommodation groove 810 from interfering with a sterilization region formed at an angle at which the sterilization light is emitted, thereby preventing a deterioration in sterilization efficiency.

The dust storage module 300 will be described below in detail with reference to FIGS. 8 and 9.

FIG. 8 is an exploded perspective view of the dust storage module 300, and FIG. 9 is a view illustrating a state in which a transmission panel 340 is coupled to a lower plate 330.

The dust storage module 300 may include the dust bag 310, an upper plate 320, and the lower plate 330.

When the suction force is generated by the dust collecting motor 200, a volume of the dust bag 310 is increased, such that the dust may be accommodated in the dust bag 310. To this end, the dust bag 310 may be made of a material that transmits air but does not transmit foreign substances such as dust. For example, the dust bag 310 may be made of a non-woven fabric material and have a hexahedral shape when the dust bag 310 has an increased volume.

When a gas flow is formed by the suction force of the dust collecting motor 200, the air, which contains foreign substances and flows from the inside of the dust bin 2160 of the cleaner 10, moves into the dust bag 310 through the suction flow path 700 and then moves out of the dust bag 310 while leaving the foreign substances in the dust bag 310.

Next, the upper plate 320 may be coupled to an outer upper surface of the dust bag 310 and inserted into the dust storage housing 800 in a sliding manner. The upper plate 320 may have a rectangular shape. In addition, the upper plate 320 may be fitted with and inserted into the dust storage housing 800 by sliding in a direction from the first outer wall surface 110 to the third outer wall surface 130 of the housing 100. To this end, protrusion portions 321 may be provided at two opposite lateral ends of the upper plate 320. In other words, in the state in which the dust storage module 300 is coupled to the dust storage housing 800, the protrusion portions 321 may include a first protrusion 321a disposed at a side of the second outer wall surface 120 of the housing 100, and a second protrusion 321b disposed at a side of the fourth outer wall surface 140 of the housing 100. The first protrusion 321a may have a 'L' shape. In addition, when an imaginary line, which connects a center point of an edge of the dust bag 310 disposed at the side of the first outer wall surface 110 of the housing 100 to a center point of an edge of the dust bag 310 disposed at the side of the third outer wall surface 130 of the housing 100, is L1, the second protrusion 321b and the first protrusion 321a may be symmetric with respect to L1.

Meanwhile, the dust storage module 300 may be coupled in the dust storage housing 800. To this end, a rail-shaped structure may be provided on an upper surface in the dust storage housing 800 and guide the protrusion portions 321 of the upper plate 320 so that the upper plate 320 is inserted by sliding.

Next, the lower plate 330 may be coupled to an upper surface in the dust bag 310. In addition, the transmission panel 340 may be coupled to the lower plate 330.

When the dust storage module 300 is coupled in the housing 100, the transmission panel 340 is disposed at a position corresponding to a position at which the sterilization module 400 to be described below is disposed. That is, the sterilization module 400 and the transmission panel 340 are disposed to face each other when the upper plate 320 is inserted into the dust storage housing 800 and the dust storage module 300 is coupled in the housing 100.

In addition, the transmission panel 340 is made of a material that may transmit the sterilization light, emitted from the sterilization module 400, toward the inside of the dust bag 310. For example, the transmission panel 340 may be made of polymethylmethacrylate (PMMA).

During a process of sucking the dust into the dust bag 310 using a high suction force, the scattering dust swirls in all directions in the dust bag 310. Even though the swirl of dust decreases in the dust bag 310 as the process of sucking the dust ends, the dust may slightly float in the dust bag 310. Therefore, the dust is consistently attached to a lower surface of the transmission panel 340 directed toward the inside of the dust bag 310. The dust attached to the transmission panel 340 decreases transmittance of the transmission panel 340 over time, thereby degrading the sterilization efficiency of the sterilization module 400.

According to the cleaner station 10 according to the embodiment of the present disclosure, the dust storage module 300 is detachably coupled in the cleaner station 10, and the dust storage module 300 includes the transmission panel 340 that transmits the sterilization light. Therefore, the transmission panel 340, together with the dust bag 310, may also be defined as a consumable component and replaceable. In other words, the transmission panel 340 to which the dust is attached may be periodically replaced with a new product. Therefore, it is possible to prevent a decrease in transmittance of the transmission panel 340 and maintain the sterilization performance of the sterilization module 400 without degrading the sterilization performance.

Meanwhile, referring to FIG. 8, the dust storage module 300 may further include a sealing plate 350 and a sliding plate 360.

The sealing plate 300 may be provided between the upper plate 320 and the dust bag 310 and seal the dust bag 310.

The sliding plate 360 may be coupled to an upper portion of the upper plate 320 and slide relative to the upper plate 320. The sliding plate 360 may serve as a handle at the time of separating the dust bag 310 from the dust bag housing 800.

The sterilization module 400 will be described below with reference to FIGS. 7, 8, and 10.

FIG. 10 is a view illustrating a configuration of the sterilization module 400 and a state in which the sterilization light is emitted from the sterilization module 400.

The sterilization module 400 is configured to sterilize the dust captured in the dust storage module 300. Referring to FIG. 10, the sterilization module 400 may include a light source 410 configured to emit the sterilization light, and a protection panel 420 disposed below the light source 410 and configured to protect the light source 410.

In this case, the light source 410 may include one or more light-emitting diodes (LEDs) capable of emitting the sterilization light having sterilizing power for removing bacteria. The sterilization light emitted from the light source 410 may have a wavelength that varies depending on types of light-emitting diodes.

For example, the light source 410 may be a light-emitting diode that emits ultraviolet rays within UV-C wavelength ranges. The ultraviolet rays are divided into UV-A rays (315 nm to 400 nm), UV-B rays (280 nm to 315 nm), and UV-C rays (200 nm to 280 nm) based on the wavelengths. The ultraviolet ray in the UV-C region may inhibit the proliferation of microorganisms by damaging DNA double helices of the microorganisms.

Alternatively, as another example, the light source 410 may be a light-emitting diode that emits visible light with a wavelength of 405 nm. The blue light having a wavelength of 405 nm has a wavelength in a boundary region between the visible ray and the ultraviolet ray and has proved sterilizing power.

To prevent damage to the light source 410, the protection panel 420 may be disposed below the light source 410 and spaced apart from the light source 410 at a predetermined distance. In this case, the protection panel 420 may be made of a material that maximize the transmittance of the light source 410. For example, the protection panel 420 may be made of quartz. It is known that the quartz does not hinder the transmission of the ultraviolet rays in the UV-C region.

Meanwhile, referring back to FIG. 7, the cleaner station 10 may further include a first mounting portion 930 on which the light source 410 is mounted, and a second mounting portion 950 on which the protection panel 420 is mounted. The first mounting portion 930 and the second mounting portion 950 may be coupled to the accommodation groove 810 in the state in which the first mounting portion 930 and the second mounting portion 950 are respectively mounted on the light source 410 and the protection panel 420. As described above, the light source 410 and the protection panel 420 are accommodated in the accommodation groove 810, such that the sterilization light may be emitted through the opening portion 815 of the accommodation groove 810 to sterilize the inside of the dust bag 310.

The cleaner station 10 according to the embodiment of the present disclosure has the sterilization module 400 that sterilizes the dust storage module 300 to prevent bacteria from proliferating in the dust storage module 300, thereby hygienically managing the dust storage module 300 that stores, for a long period of time, the dust sucked from the dust bin 1260 of the cleaner 10.

Meanwhile, as described above, the sterilization module 400 and the transmission panel 340 are disposed to face each other when the dust storage module 300 is coupled in the housing 100. More specifically, the light source 410, the protection panel 420, and the transmission panel 340 are sequentially disposed from above to below.

In this case, in the embodiment of the present disclosure, the protection panel 420 disposed below the light source 410 may be made of quartz, and the transmission panel 430, which may be periodically replaceable, may be made of PMMA and disposed below the protection panel 420.

That is, the expensive quartz may be used semipermanently, and the relatively inexpensive PMMA may be replaced together with the dust bag 310. Therefore, it is possible to reduce costs in terms of manufacture, maintenance, and repair.

Referring back to FIG. 8, communication holes H1a, H2a, H3a, H4a, and H5a may be provided in the dust bag 310, the upper plate 320, the lower plate 330, the sealing plate 350, and the sliding plate 360, respectively, to allow the inside of the suction flow path 700 and the inside of the dust bag 310 to communicate with each other.

In addition, transmission holes H1b, H2b, H4b, and H5b may be provided in the dust bag 310, the upper plate 320, the sealing plate 350, and the sliding plate 360, respectively, so as not to hinder the transmission of the sterilization light.

In this case, the communication holes H1a, H2a, H3a, H4a, and H5a provided in the respective components each have a shape corresponding to a shape of the suction flow path 700. The communication holes H1a, H2a, H3a, H4a, and H5a are disposed at positions facing the suction flow path 700 when the dust storage module 300 is coupled in the housing 100. For example, the communication holes H1a, H2a, H3a, H4a, and H5a may each have a circular shape.

In addition, the transmission holes H1b, H2b, H4b, and H5b provided in the respective components each have a shape corresponding to a shape of the accommodation groove 810. The transmission holes H1b, H2b, H4b, and H5b are disposed at positions facing the sterilization module 400 when the dust storage module 300 is coupled in the housing 100. For example, the transmission holes H1b, H2b, H4b, and H5b may each have a quadrangular shape.

In addition, the communication holes H1a, H2a, H3a, H4a, and H5a and the transmission holes H1b, H2b, H4b, and H5b, which are provided in the respective components, may be disposed to be spaced apart from one another at predetermined distances so as not to interfere with one another. When the dust storage module 300 is coupled in the housing 100, L1 may pass through centers of communication holes H11, H12, H13, H14, and H15 and centers of transmission holes H21, H22, H23, H24, and H25.

FIGS. 11A and 11B are schematic views illustrating an arrangement relationship between the suction flow path 700 and the sterilization module 400 in the cleaner station 10 according to the embodiment of the present disclosure.

First, referring to FIG. 11B, in the cleaner station 10 according to the embodiment of the present disclosure, the sterilization module 400 may be disposed in such a manner that an imaginary connection line connecting a center of the upper surface of the dust bag 310 and a center of the lower surface of the dust bag 310 passes through an approximate center of the light source 410.

More specifically, the center of the upper surface of the dust bag 310 means an intersection point of two diagonal lines made by connecting vertices facing one another in a diagonal direction on the upper surface of the dust bag 310. The center of the lower surface of the dust bag 310 means an intersection point of two diagonal lines made by connecting vertices facing one another in a diagonal direction on the lower surface of the dust bag 310.

That is, when an imaginary connection line connecting the center of the upper surface of the dust bag 310 and the center of the lower surface of the dust bag 310 is L2, the light source 410 may be disposed in such a manner that L2 passes through the center of the light source 410.

The center of the light source 410 may mean an optical axis of the light source 410. In other words, the center of the light source 410 may mean a central axis of the light-emitting element. For example, the optical axis of the light source 410 may mean a central axis of a directional angle. In this case, the directional angle indicates a range in which the light-emitting element emits light. The unit of the directional angle is degree (°).

FIG. 11B illustrates that the sterilization light is emitted from the sterilization module 400 at a directional angle of 120°.

Referring to FIG. 11A, it is assumed that in the state in which the dust bag 310 is coupled to the housing 100, an imaginary connection line is L3 that connects a center point of the edge of the dust bag 310 positioned at the side of the first outer wall surface 110 of the housing 100 and a center point of the edge positioned at the side of the third outer wall surface 130 of the housing 100, and an imaginary connection line is L4 that connects a center point of the edge positioned at the side of the second outer wall surface 120 of the housing 100 and a center point of the edge positioned at the side of the fourth outer wall surface 140 of the housing 100.

The center of the light source 410 may be disposed on an intersection point between L3 and L4 (also called the center of the upper surface of the dust bag 310).

Meanwhile, for the arrangement described above, it can be seen that the suction flow path 700 needs to be eccentrically disposed at one side spaced apart from the center of the upper surface of the dust bag 310 at a predetermined distance. For example, the suction flow path 700 may be eccentrically disposed at the side of the first outer wall surface 110 of the housing 100 in the state in which the dust bag 310 is coupled to the housing 100. In this case, as illustrated in FIG. 2, the suction flow path 700 may have a shape bent toward one side at which the suction flow path 700 is eccentrically disposed.

In contrast, referring to FIG. 12A, it is assumed that the suction flow path 700 is disposed on the intersection point between the L3 and the L4.

In this case, the sterilization module 400, instead of the suction flow path 700, is inevitably disposed eccentrically at one side spaced apart from the center of the upper surface of the dust bag 310 at a predetermined distance.

In this case, because the sterilization light emitted from the light source 410 propagates toward the periphery of the optical axis at a predetermined angle (e.g., 120°), a large dead zone, which is not affected by the sterilization light, is formed at one side opposite to one side at which the sterilization module 400 is eccentrically disposed. The increase in dead zone degrades the sterilization effect to that extent.

Therefore, to minimize the dead zone, the cleaner station 10 according to the embodiment of the present disclosure has the proposed structure in which the imaginary connection line L2, which connects the center of the upper surface of the dust bag 310 and the center of the lower surface of the dust bag 310, passes through the approximate center of the light source 410.

Therefore, the sterilization light emitted from the light source 410 propagates toward the periphery of the optical axis at a predetermined angle, which makes it possible to minimize a dead zone formed at an upper edge of the dust bag 310 and maximize the sterilization efficiency.

On the contrary, the arrangement of the suction flow path 700 and the sterilization module 400 may be variously modified as necessary. Various embodiments of the arrangement relationship between the suction flow path 700 and the sterilization module 400 will be described below. However, it is noted that the present disclosure is not limited only to the following embodiments of the arrangement relationship.

FIGS. 12A to 14B are views illustrating various embodiments of the arrangement relationship between the suction flow path 700 and the sterilization module 400.

For example, referring to FIGS. 12A and 12B, the suction flow path 700 may be disposed on the intersection point between L3 and L4, and the center of the light source 410 of the sterilization module 400 may be disposed on L3 and spaced apart from the suction flow path 700 at a predetermined distance toward the first outer wall surface 110 of the housing 100 so as not to interfere with the suction flow path 700.

In consideration of the above-mentioned arrangement, there is a problem in that a large dead zone may be formed at the periphery of the upper edge of the dust bag 310 at the side of the first outer wall surface 110 as described above. To maximally minimize the size of the dead zone, the sterilization module 400 and the suction flow path 700 may be spaced apart from each other so as not to interfere with each other, and a spacing distance between the sterilization module 400 and the suction flow path 700 may be as short as possible.

As another example, referring to FIGS. 13A and 13B, the suction flow path 700 may be disposed on the intersection point between L3 and L4, and the center of the light source 410 of the sterilization module 400 may be disposed on L3 and spaced apart from the suction flow path 700 at a predetermined distance toward the third outer wall surface 130 of the housing 100 so as not to interfere with the suction flow path 700.

In consideration of the above-mentioned arrangement, there is a problem in that a large dead zone may be formed at the periphery of the upper edge of the dust bag 310 at the side of the third outer wall surface 130. To maximally minimize the size of the dead zone, the sterilization module 400 and the suction flow path 700 may be spaced apart from each other so as not to interfere with each other, and a spacing distance between the sterilization module 400 and the suction flow path 700 may be as short as possible.

As another example, referring to FIGS. 14A and 14B, the suction flow path 700 may be disposed on the intersection point between L3 and L4, two sterilization modules 400 (also called a first sterilization module 400a and a second sterilization module 400b) may be provided, a center of a light source 410a of the first sterilization module 400a may be disposed on L3 and spaced apart from the suction flow path 700 at a predetermined distance toward the first outer wall surface 110 so as not to interfere with the suction flow path 700, and a center of a light source 410b of the second sterilization module 400a may be disposed on L3 and spaced apart from the suction flow path 700 at a predetermined distance toward the third outer wall surface 130 so as not to interfere with the suction flow path 700. That is, the first sterilization module 400a and the second sterilization module 400b may be disposed opposite to each other based on L4. Meanwhile, the first sterilization module 400a and the second sterilization module 400b may be disposed at positions symmetric to each other based on L4 which is a reference line.

In consideration of the above-mentioned arrangement, an interval between the first sterilization module 400a and the second sterilization module 400b may be determined as an interval for minimizing a size of the dead zone at the side of the first outer wall surface 110 and a size of the dead zone at the side of the third outer wall surface 130.

Meanwhile, referring back to FIGS. 7 and 10, an area of the transmission panel 340 may be larger than an area of the protection panel 420. In this case, the area of the transmission panel 340 may be determined as an area capable of receiving the directional angle of the light source 410.

Since the area of the transmission panel 340 may be larger than the area of the protection panel 420, the transmission panel 340 may transmit the entire sterilization light emitted at the directional angle of the light source 410, as illustrated in FIG. 10, which makes it possible to optimize the sterilization efficiency.

Results of experiments performed on the sterilization effect of the sterilization module will be described below with reference to FIG. 15 and Tables 1 to 3.

FIG. 15 illustrates an experimental device used to measure the transmittance of the sterilization light of the transmission panel 340 made of PMMA.

An experimental chamber having an illuminance measurement sensor provided on a bottom surface therein was prepared. First, an illuminance value on the bottom in the chamber was measured using the illuminance sensor under a condition in which no PMMA was present on an outer upper portion of the chamber. Next, an illuminance value on the bottom in the chamber was measured using the illuminance sensor under a condition in which PMMA It was provided on the outer upper portion of the chamber and UV-C sterilization light was emitted to penetrate PMMA. The transmittance of the UV-C sterilization light when the thickness of the PMMA was 1t compared to the case in which no PMMA was present may be obtained using a ratio between the two measured values.

According to the experimental result, the illuminance value was measured as 1.50 mW/cm$^2$ when no PMMA was present, and the illuminance value of the sterilization light penetrating the PMMA when the PMMA was present was measured as 0.91 mW/cm$^2$. Therefore, the transmittance of the PMMA was calculated as 60.7%.

The following Table 1 shows a result of testing the transmittance when both the transmission panel 340 and the protection panel 420 are present.

TABLE 1

| mW/cm$^2$ | 3 mW | 4 mW |
|---|---|---|
| Initial Illuminance Value (Air Gap of 6 mm) | 0.9 mW/cm$^2$ | 0.97 mW/cm$^2$ |
| Protection Panel 2t / Transmission Panel 1t | 0.52 mW/cm$^2$ | 0.54 mW/cm$^2$ |
| Transmittance | 57.8% | 55.7% |

The transmission panel 340 was made of PMMA, the protection panel 420 was made of quartz, the protection panel 420 had a thickness of 2t, the transmission panel 340 had a thickness of 1t, a spacing distance between the protection panel 420 and the transmission panel 340 was 3 mm.

The light-emitting diode emitting UV-C ultraviolet rays was selected as the light source 410, and the transmittance was measured when the illuminance values were 3 mW and the 4 mW. First, the illuminance was measured when only an air gap of 6 mm was present under a condition in which there was neither transmission panel 340 nor protection panel 420. In this case, the illuminance was measured as 0.9 mW/cm$^2$ in the case of the 3 mW light source, and the illuminance was measured as 0.97 mW/cm$^2$ in the case of the 4 mW light source.

Next, the illuminance was measured under a condition in which the transmission panel 340 and the protection panel 420 were provided and a spacing distance between the transmission panel 340 and the protection panel 420 was 6 mm. In this case, the illuminance was measured as 0.52 mW/cm$^2$ in the case of the 3 mW light source 410, and the illuminance was measured as 0.54 mW/cm$^2$ in the case of the 4 mW light source 410.

Consequently, it can be seen that when the protection panel 420 and the transmission panel 340 are provided and the light source 410 emits light that penetrates the respective panels, the transmittance is 57.8% in the case of the 3 mW light source 410, and the transmittance is 55.7% in the case of the 4 mW light source 410.

The following Table 2 shows a result of a transmittance test when the sterilization light emitted from the light source 410 is visible light having a wavelength of 405 nm and both the transmission panel 340 and the protection panel 420 are present.

TABLE 2

| Initial Illuminance Value | Protection Panel (Quartz) 1t/Transmission Panel (PMMA) 1t | Protection Panel (PMMA) 1t/Transmission Panel (PMMA) 1t |
|---|---|---|
| 0.17 mW/cm$^2$ | 0.17 mW/cm$^2$ | 0.17 mW/cm$^2$ |

The transmission panel 340 was made of PMMA, the protection panel 420 was made of quartz and PMMA, the protection panel 420 and the transmission panel 340 each had a thickness of 1t, a spacing distance between the protection panel 420 and the transmission panel 340 was 3 mm. Referring to Table 2, it can be seen that when the sterilization light emitted from the light source 410 is visible light having a wavelength of 405 nm, the transmittance is 100% regardless of the material of the protection panel 420.

The following Table 3 shows sterilizing power when UV-C sterilization light was emitted in the chamber of the experimental device illustrated in FIG. 15 under various conditions.

TABLE 3

| | Control Group | 2 mW Protection Panel (Quartz) 2t/Transmission Panel (PMMA) 1t | 3 mW Protection Panel (Quartz) 2t/Transmission Panel (PMMA) 1t | 4 mW Protection Panel (Quartz) 2t/Transmission Panel (PMMA) 1t | 2 mW Protection Panel and No Transmission Panel | 3 mW Protection Panel and No Transmission Panel |
|---|---|---|---|---|---|---|
| Number of *E. coli* | 1.164 | 0 | 0 | 0 | 0 | 0 |
| Number of *S. aureus* | 1.096 | 0 | 0 | 0 | 0 | 0 |

As shown in Table 3 showing the results, whether the bacteria had grown and died was observed after emitting the UV-C sterilization light in a case in which the bacteria were attached to an edge of the chamber under the experiment condition.

Consequently, under various experimental conditions shown in Table 3, the growth of *E. coli* and *S. aureus* could not be observed when the UV-C sterilization light was emitted for one hour. The sterilization effect of about 99.99% was observed in comparison with samples in a control group.

As described above, the cleaner station according to the present disclosure has the sterilization module that may sterilize the dust storage module to prevent the proliferation of bacteria in the dust storage module, thereby hygienically managing the dust storage module.

In addition, according to the cleaner station according to the present disclosure, the dust storage module is detachably coupled in the cleaner station, the transmission panel, which transmits the sterilization light, is coupled to the dust storage module, and the transmission panel is provided as a replaceable consumable component. There is concern that dust may be attached to the transmission panel during the suction process, which may degrade transmission efficiency. However, since the transmission panel is consistently replaced, it is possible to maintain the performance of the sterilization module for sterilizing the dust storage module without degrading the performance.

In addition, according to the cleaner station according to the present disclosure, the imaginary connection line, which connects the center of the upper surface of the dust bag and the center of the lower surface of the dust bag, passes through the approximate center of the light source that emits the sterilization light. Therefore, it is possible to minimize the dead zone which is a region that a range of the sterilization light cannot reach.

While the specific embodiments of the present disclosure have been described and illustrated, it is obvious to those skilled in the art that the present disclosure is not limited to the aforementioned embodiments and may be variously changed and modified without departing from the spirit and the scope of the present disclosure. Therefore, the scope of the present disclosure should be determined by the technical spirit of the appended claims instead of being determined by the described embodiment.

DESCRIPTION OF REFERENCE NUMERALS

1: Dust removing system
10: Cleaner station
100: Housing
110: First outer wall surface
115: Coupling part
120: Second outer wall surface
130: Third outer wall surface
140: Fourth outer wall surface
150: Floor support part
200: Dust collecting motor
300: Dust storage module
310: Dust bag
320: Upper plate
321: Protrusion portion
321a: First protrusion
321b: Second protrusion
330: Lower plate
340: Transmission panel
350: Sealing plate
360: Sliding plate
400: Sterilization module
410: Light source
420: Protection panel
500: Cover opening unit
510: Push protrusion
520: Cover opening gear
521: First cover opening gear
522: Second cover opening gear
600: Door unit
610: Door
620: Door arm
621: First door arm
622: Second door arm
630: Door motor
700: Suction flow path
800: Dust storage housing
810: Accommodation groove
815: Opening portion
815a: Inclined surface
930: First mounting portion
950: Second mounting portion
20: Cleaner
2100: Cleaner main body
2110: Suction part
2120: Dust separating part
2130: Suction motor
2140: Handle
2150: Battery housing
2160: Dust bin
2161: Discharge cover
2161a: Cover main body
2161b: Hinge part
2161c: Coupling lever

The invention claimed is:

1. A cleaner station comprising:
a housing configured to receive a cleaner;
a dust collecting motor that is accommodated in the housing and that is configured to generate a suction force for suctioning a foreign substance out of a dust bin of the cleaner;
a dust storage module configured to, based on the dust collecting motor being operated, receive the foreign substance from the dust bin; and
a sterilization module configured to sterilize the foreign substance received in the dust storage module,
wherein the dust storage module comprises:
a transmission panel configured to transmit sterilization light emitted by the sterilization module,
a dust bag that is configured to, based on the dust collecting motor generating the suction force to accommodate the foreign substance, increase volume, and
a lower plate that is coupled to the transmission panel and that is coupled to an inner upper surface of the dust bag,
wherein the dust storage module is detachably coupled to the housing together with the transmission panel, and
wherein the transmission panel is configured to be detachably coupled to the lower plate.

2. The cleaner station of claim 1, wherein the sterilization module comprises:
a light source configured to emit the sterilization light, and
a protection panel that is disposed below the light source and that protects the light source.

3. The cleaner station of claim 2, wherein the light source is an ultraviolet C (UV-C) light-emitting diode (LED).

4. The cleaner station of claim 2, wherein a wavelength of the sterilization light emitted by the light source is 405 nm.

5. The cleaner station of claim 1, further comprising:
a dust storage housing that is accommodated in the housing and that defines an internal space to which the dust storage module is coupled,
wherein the dust storage housing defines an accommodation groove at a part of an outer upper surface, the part of the outer upper surface being angled toward the internal space and accommodating the sterilization module, and
wherein a lower end of the accommodation groove passes through the internal space.

6. The cleaner station of claim 5, wherein the dust storage module further comprises:
an upper plate that is coupled to an outer upper surface of the dust bag and that is configured to be inserted into the dust storage housing in a sliding manner.

7. The cleaner station of claim 6, wherein the sterilization module and the transmission panel face each other based on the upper plate being inserted into and coupled to the dust storage housing.

8. A cleaner station comprising:
a housing configured to receive a cleaner;
a dust collecting motor that is accommodated in the housing and that is configured to generate a suction force for suctioning a foreign substance out of a dust bin of the cleaner;
a dust storage module configured to, based on the dust collecting motor being operated, receive the foreign substance from the dust bin;
a dust storage housing that is accommodated in the housing and that defines an internal space to which the dust storage module is coupled; and
a sterilization module configured to sterilize the foreign substance received in the dust storage module,
wherein the dust storage module comprises:
a dust bag that is configured to, based on the dust collecting motor generating the suction force to accommodate the foreign substance, increase volume, and
a lower plate coupled to an inner upper surface of the dust bag,
wherein the sterilization module is disposed above the dust storage housing and comprises a light source configured to emit sterilization light,
wherein a connection line connecting a center of an upper surface of the dust bag and a center of a lower surface of the dust bag passes through a center of the light source,
wherein the dust storage module further comprises:
a transmission panel configured to transmit the sterilization light emitted from the sterilization module and configured to be detachably coupled to the lower plate, and
wherein the lower plate is coupled to the transmission panel.

9. The cleaner station of claim 8, wherein the sterilization module further comprises a protection panel that is disposed below the light source and that protects the light source.

10. The cleaner station of claim 9, wherein the dust storage module further comprises:
an upper plate that is coupled to an outer upper surface of the dust bag and that is configured to be inserted into the dust storage housing in a sliding manner.

11. The cleaner station of claim 10, wherein an area of the transmission panel is larger than an area of the protection panel.

12. The cleaner station of claim 10, wherein the dust storage housing defines an accommodation groove at a part of an outer upper surface, the part of the outer upper surface being angled toward the internal space and accommodating the sterilization module, and
wherein a lower end of the accommodation groove passes through the internal space.

13. The cleaner station of claim 12, wherein the sterilization module and the transmission panel face each other based on the upper plate being inserted into and coupled to the dust storage housing.

14. The cleaner station of claim 8, wherein the light source is an ultraviolet C (UV-C) light-emitting diode (LED).

15. The cleaner station of claim 8, wherein a wavelength of the sterilization light emitted by the light source is 405 nm.

16. A cleaner station comprising:
a housing configured to receive a cleaner;
a dust collecting motor that is accommodated in the housing and that is configured to generate a suction force for suctioning a foreign substance out of a dust bin of the cleaner;
a dust storage module configured to, based on the dust collecting motor being operated, receive the foreign substance from the dust bin; and
a sterilization module that is configured to sterilize the foreign substance received in the dust storage module,
wherein the dust storage module comprises:
a transmission panel configured to transmit sterilization light emitted by the sterilization module, a dust bag that is configured to, based on the dust collecting motor generating the suction force to accommodate the foreign substance, increase volume, and a lower plate that is coupled to the transmission panel and an inner upper surface of the dust bag, wherein the dust storage module is detachably coupled to the housing together with the transmission panel, wherein the sterilization module comprises a light source configured to emit the sterilization light and a protection panel that is disposed below the light source and that protects the light source, and wherein the transmission panel is configured to be detachably coupled to the lower plate.

17. The cleaner station of claim 16, wherein the light source is an ultraviolet C (UV-C) light-emitting diode (LED).

18. The cleaner station of claim 16, wherein a wavelength of the sterilization light emitted by the light source is 405 nm.

19. The cleaner station of claim 16, further comprising:

a dust storage housing that is accommodated in the housing and that defines an internal space in which the dust storage module is coupled, wherein the dust storage housing defines an accommodation groove at a part of an outer upper surface, the part of the outer upper surface being angled toward the internal space and accommodating the sterilization module, and wherein a lower end of the accommodation groove passes through the internal space.

20. The cleaner station of claim 19, wherein the dust storage module further comprises:

an upper plate that is coupled to an outer upper surface of the dust bag and that is configured to be inserted into the dust storage housing in a sliding manner.

* * * * *